US012569510B2

(12) United States Patent
Chatterjee et al.

(10) Patent No.: US 12,569,510 B2
(45) Date of Patent: Mar. 10, 2026

(54) ANTIVIRAL PRODRUGS AND PHARMACEUTICAL COMPOSITIONS THEREOF

(71) Applicant: THE SCRIPPS RESEARCH INSTITUTE, La Jolla, CA (US)

(72) Inventors: Arnab K. Chatterjee, San Diego, CA (US); Anil K. Gupta, San Diego, CA (US); Anders M. Eliasen, Los Angeles, CA (US); Sean B. Joseph, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 853 days.

(21) Appl. No.: 17/642,559

(22) PCT Filed: Sep. 11, 2020

(86) PCT No.: PCT/US2020/050511

§ 371 (c)(1),
(2) Date: Mar. 11, 2022

(87) PCT Pub. No.: WO2021/050956

PCT Pub. Date: Mar. 18, 2021

(65) Prior Publication Data

US 2022/0332751 A1 Oct. 20, 2022

Related U.S. Application Data

(60) Provisional application No. 62/898,679, filed on Sep. 11, 2019.

(51) Int. Cl.

| | |
|---|---|
| ***A61K 31/7076*** | (2006.01) |
| ***A61K 9/00*** | (2006.01) |
| ***A61K 9/10*** | (2006.01) |
| ***A61K 31/4439*** | (2006.01) |
| ***A61K 31/4985*** | (2006.01) |
| ***A61K 31/513*** | (2006.01) |
| ***A61K 31/5365*** | (2006.01) |
| ***A61K 31/675*** | (2006.01) |
| ***A61K 47/26*** | (2006.01) |
| ***A61K 47/38*** | (2006.01) |
| ***A61P 31/18*** | (2006.01) |
| ***A61P 31/20*** | (2006.01) |
| ***C07H 19/16*** | (2006.01) |

(52) U.S. Cl.

CPC ........ *A61K 31/7076* (2013.01); *A61K 9/0019* (2013.01); *A61K 9/10* (2013.01); *A61K 31/4439* (2013.01); *A61K 31/4985* (2013.01); *A61K 31/513* (2013.01); *A61K 31/5365* (2013.01); *A61K 31/675* (2013.01); *A61K 47/26* (2013.01); *A61K 47/38* (2013.01); *A61P 31/18* (2018.01); *A61P 31/20* (2018.01); *C07H 19/16* (2013.01)

(58) Field of Classification Search

None

See application file for complete search history.

(56) References Cited

U.S. PATENT DOCUMENTS

| | | | |
|---|---|---|---|
| 5,192,749 | A | 3/1993 | O-Yang et al. |
| 5,283,067 | A | 2/1994 | Geller et al. |
| 6,875,751 | B2 | 4/2005 | Imbach et al. |
| 7,339,053 | B2 | 3/2008 | Kohgo et al. |
| 8,569,478 | B2 | 10/2013 | Du et al. |
| 8,835,615 | B2 | 9/2014 | Chang |
| 2003/0083306 | A1 | 5/2003 | Imbach et al. |
| 2005/0215512 | A1 | 9/2005 | Kohgo et al. |
| 2009/0274686 | A1 | 11/2009 | Or et al. |
| 2011/0021454 | A1 | 1/2011 | Du et al. |
| 2016/0129122 | A1 | 5/2016 | Milne et al. |
| 2018/0002366 | A1 | 1/2018 | Girijavallabhan et al. |
| 2019/0171285 | A1 | 6/2019 | Sulai et al. |
| 2019/0185508 | A1 | 6/2019 | Alexandre et al. |
| 2022/0323476 | A1 | 10/2022 | Chatterjee et al. |
| 2025/0101057 | A1 | 3/2025 | Shi |
| 2025/0136603 | A1 | 5/2025 | Chtchemelinine |

FOREIGN PATENT DOCUMENTS

| | | | |
|---|---|---|---|
| CN | 101177442 | | 5/2008 |
| CN | 106795199 | | 5/2017 |
| CN | 108289931 | | 7/2018 |
| CN | 114502175 | | 5/2022 |
| EA | 202192433 | | 12/2021 |
| EP | 0605700 | A1 | 7/1994 |
| EP | 1589026 | | 10/2005 |
| EP | 2177527 | A1 | 4/2010 |
| JP | 2003-520776 | A | 7/2003 |
| JP | 2011-256173 | A | 12/2011 |
| JP | 2022-515857 | A | 2/2022 |
| JP | 2022-547978 | A | 11/2022 |
| NO | 2020178767 | A1 | 9/2020 |
| RU | 2017133011 | | 4/2019 |
| WO | WO 2000069876 | | 11/2000 |
| WO | WO 2000069877 | | 11/2000 |
| WO | WO 2010075517 | | 7/2010 |
| WO | WO 2015143712 | | 10/2015 |
| WO | 2017053216 | A1 | 3/2017 |
| WO | WO 2017100108 | | 6/2017 |
| WO | WO 2018002366 | | 1/2018 |
| WO | WO 2019113462 | | 6/2019 |
| WO | 2019171285 | A1 | 9/2019 |
| WO | 2020031131 | A1 | 2/2020 |

(Continued)

OTHER PUBLICATIONS

Agarwal et al., "Synthesis and Biological Evaluation of Fatty Acyl Ester Derivatives of (-)-2',3'-Dideoxy-3'-thiacytidine," Journal of Medicinal Chemistry, Apr. 25, 2012, 55(10):4861-71.

(Continued)

*Primary Examiner* — Katherine Peebles

(74) *Attorney, Agent, or Firm* — Fish & Richardson P.C.

(57) ABSTRACT

Diesters of 4'-ethynyl-2-fluoro-2'-deoxyadenosine and aqueous parenteral suspensions thereof provide extended in vivo viral suppression of human immunodeficiency virus (HIV).

2 Claims, 15 Drawing Sheets

(56) References Cited

FOREIGN PATENT DOCUMENTS

| | | | |
|---|---|---|---|
| WO | WO 2020178767 | | 9/2020 |
| WO | WO 2021021717 | A1 | 2/2021 |
| WO | WO 2021050956 | | 3/2021 |
| WO | WO 2021050961 | A1 | 3/2021 |
| WO | WO 2025006582 | A1 | 1/2025 |
| WO | WO 2025006586 | A1 | 1/2025 |

OTHER PUBLICATIONS

Basic Concepts in Medicinal Chemistry, 2nd ed., Harrold et al. (eds.), 2018, Chapter 2, 46 pages.
Chilean Office Action in CL Appln. No. 202200587, dated Jul. 3, 2023, 41 pages (with English translation).
Chilean Office Action in CL Appln. No. 202200601, dated Jul. 3, 2023, 40 pages (with English translation).
Chinese Office Action in CN Appln. No. 202080075497.7, dated Jul. 22, 2023, 13 pages (with English translation).
Chinese Office Action in CN Appln. No. 202080077922.6, dated Jul. 26, 2023, 13 pages (with English translation).
Eurasian Office Action in EA Appln. No. 202290768, dated Dec. 23, 2022, 6 pages (with English translation).
Eurasian Office Action in EA Appln. No. 202290814, dated Jan. 13, 2023, 8 pages (with English translation).
Extended European Search Report in EP Appln. No. 20862707.5, dated Aug. 29, 2023, 12 pages.
Høyem et al., "Didanosine ester prodrugs: Synthesis, albumin binding properties and pharmacokinetic studies in rats," European Journal of Medicinal Chemistry, Oct. 2009, 44(10):3874-3879.
Indonesian Office Action in ID Appln. No. P00202204197, dated Nov. 13, 2023, 6 pages (with English translation).
Office Action in U.S. Appl. No. 18/233,959, dated Dec. 27, 2023, 12 pages.
Parang et al., "Novel Approaches for Designing 5'-O-Ester Prodrugs of 3'-Azido-2'3'-dideoxythymidine (AZT)," Current Medicinal Chemistry, Oct. 2000, 7(10): 995-1039.
PCT International Preliminary Report on Patentability in International Appln. No. PCT/US2020/050511, dated Mar. 15, 2022, 6 pages.
PCT International Preliminary Report on Patentability in International Appln. No. PCT/US2020/050519, dated Mar. 15, 2022, 6 pages.
PCT International Search Report and Written Opinion issued in International Appln. No. PCT/US2020/050511, dated Dec. 8, 2020, 8 pages.
PCT International Search Report and Written Opinion issued in International Appln. No. PCT/US2020/050519, dated Feb. 2, 2021, 9 pages.
PubChem, "Compound Summary for CID 139466901, [(2R,3S,5R)-5-(6-amino-2-fluoro-purin-9-yl)-2-ethynyl-3-hydroxy-tetrahydrofuran-2-yl]methyl acetate," Nov. 2, 2019, 12 pages.
Qidong, "Medicinal Chemistry," China Medical Science & Technology Press, You (ed.), Feb. 2011, p. 570, 3 pages (with English translation).
Saudi Arabian Office Action in SA Appln. No. 522431901, dated Sep. 24, 2023, 5 pages.
Sriram et al., "Synthesis of stavudine amino acid ester prodrugs with broad-spectrum chemotherapeutic properties for the effective treatment of HIV/AIDS," Bioorganic & Medicinal Chemistry Letters, Mar. 2004, 14(5): 1085-1087.
U.S. Appl. No. 17/642,552, filed Mar. 11, 2022, Arnab Kumar Chatterjee.
U.S. Appl. No. 18/233,959, filed Aug. 15, 2023, Arnab K. Chatterjee.
Barrett, S.E. et al., Extended-Duration MK-8591-Eluting Implant as a Candidate for HIV Treatment and Prevention, Antimicrobial Agents and Chemotherapy 62 (10), 1-13 (2018).
Kageyama, M. et al., Enantioselective Total Synthesis of the Potent Anti-HIV Nucleoside EFdA, Organic Letters 13 (19), 5264-5266 (2011).
Nakata, H. et al., Activity Against Human Immunodeficiency Virus Type 1, Intracellular Metabolism, and Effects on Human DNA Polymerases of 4'-Ethynyl -2-Fluoro-2'-Deoxyadenosine, Antimicrobial Agents and Chemotherapy 51 (8), 2701-2708 (2007).
Rautio, J. et al., Prodrugs: Design and Clinical Applications, Nature Reviews 7, 255-270 (2008).
Foster, "Deuterium Isotope Effects in Studies of Drug Metabolism," Trends Pharmacol. Sci., Jan. 1984, S(12):524-527.
Jiang et al., "Anti-HIV new drug: D-D4FC," Chin. J. New Drugs Clin. Rem., May 5, 2008, 5(27)369-372 (with English Abstract).
Jones et al., "Di-and triester prodrugs of the varicella-zoster antiviral agent 6-methoxypurine arabinoside," J. Med. Chem., Jan. 1992, 35(1):56-63 (abstract only).
Kirby et al., "Effects of Substitutions at the 4' and 2 Positions on the Bioactivity of 4'-Ethynyl-2-Fluoro-2'-Deoxyadenosine," Antimicrobial Agents and Chemotherapy, Dec. 2013, 57(12):6254-6264.
Markowitz et al., "4'-Ethynyl-2-fluoro-2'-deoxyadenosine, MK-8591: a novel HIV-1 reverse transcriptase translocation inhibitor," Curr. Opin. HIV AIDS, Jul. 2018, 13(4): 294-299.
McLaughlin et al., "Enantioselective Synthesis of 4'-Ethynyl-2-fluoro-2'-deoxyadenosine (EFdA) via Enzymatic Desymmetrization," Organic Letters, Feb. 6, 2017, 19(4):926-929.
Rai et al., "Emerging reverse transcriptase inhibitors for HIV-1 infection," Expert Opin. Emerg. Drugs, Apr. 3, 2018, 23(2):149-157.
ARIPO Office Action in ARIPO Appln. No. AP/P/2022/014309, dated Oct. 21, 2024, 5 pages.
ARIPO Office Action in ARIPO Appln. No. AP/P/2022/014310, dated Oct. 21, 2024, 5 pages.
Chilean Office Action in CL Appln. No. 202200601, dated Jul. 17, 2024, 40 pages (with English translation).
Chinese Notice of Grant in CN Appln. No. 202080077922.6, dated Aug. 1, 2024, 10 pages (with English translation).
Dominican Republic Office Action in DO Appln. No. P2022-0055, dated Aug. 14, 2024, 9 pages (with English translation).
Egyptian Office Action in EG Appln. No. PCT281/2022, dated Sep. 25, 2024, 14 pages (with English translation).
Hearing Notice in IN Appln. No. 202247020416, dated Nov. 4, 2024, 2 pages.
Israeli Office Action in Israeli Appln. No. 290919, dated Jul. 30, 2024, 4 pages.
Japanese Office Action in Japanese Appln. No. 2022-515857, mailed on Nov. 12, 2024, 8 pages (with English translation).
Japanese Office Action in Japanese Appln. No. 2022-515860, mailed on Nov. 8, 2024, 4 pages (with English translation).
Mexican Office Action in Mexican Appln. No. MX/a/2022/002899, dated Oct. 25, 2024, 10 pages (with machine translation).
Fukuyama, K. et al., Synthesis of EFdA via a Diastereoselective Aldol Reaction of a Protected 3-Keto Furanose, Organic Letters 17 (4), 828-831, Publication year: 2002.
Indian Office Action in IN Appln. No. 202247020416, dated Feb. 6, 2024, 5 pages.
Indonesian Office Action in ID Appln. No. P00202204210, dated Nov. 21, 2023, 6 pages (with English translation).
Sun et al., "[Progress in clinical and basic research on anti-HIV drug resistance]," China Journal of AIDS and STDs, Feb. 2011, 17(1):81-84 (with English Abstract).
Chinese Office Action in Chinese Appln. No. 202080075497.7, dated Mar. 18, 2024, 11 pages (with English translation).
Extended European Search Report in EP Appln. No. 20862704.2, dated Mar. 18, 2024, 9 pages.
Russian Office Action in Russian Appln. No. 2022109055, dated Feb. 9, 2024, 19 pages (with English translation).
Taylor, "Improved passive oral drug delivery via prodrugs," Adv Drug Deliv Rev, vol. 19, pp. 131-148. (Year: 1996).
ARIPO Office Action in ARIPO Appln. No. AP/P/2022/013888, dated May 2, 2024, 4 pages.
Eurasian Office Action in EA Appln. No. 202290814, dated Feb. 14, 2024, 4 pages (with English translation).

(56) References Cited

OTHER PUBLICATIONS

Saudi Arabian Office Action in SA Appln. No. 522431901, dated Mar. 11, 2024, 6 pages (English translation only).
Ukrainian Office Action in Ukrainian Appln. No. a202201150, dated Mar. 29, 2024, 5 pages (with English translation).
Chilean Office Action in Chilean Appln. No. 202200587, dated Jul. 2, 2024, 34 pages (with English translation).
Israeli Office Action in Israeli Appln. No. 290861, dated Jun. 19, 2024, 3 pages.
Russian Office Action in Russian Appln. No. 2022108749, dated May 9, 2024, 24 pages (with English translation).
Ukrainian Office Action in Ukrainian Appln. No. a202201149, dated May 20, 2024, 7 pages (with English translation).
Vietnamese Office Action in Vietnamese Appln. No. 1-2022-01996, dated Apr. 25, 2024, 4 pages (with English translation).
Mexican Office Action in Mexican Appln. No. MX/a/2022/002899, dated Apr. 16, 2025, 10 pages (with machine translation).
Mexican Office Action in Mexican Appln. No. MX/a/2022/002899, dated Jan. 27, 2025, 8 pages (with machine translation).
Office Action for Aripo Appln. No. AP/P/2022/013887, mailed May 9, 2025, 4 pages.
Office Action for Ukrainian Appln. No. a202201149, dated Mar. 19, 2025, 3 pages (with English translation).
Office Action for United Arab Emirates Appln. No. P6000438/2022, dated Mar. 21, 2025, 6 pages.
Office Action in Saudi Arabian Appln. No. dated Mar. 12, 2025, 15 pages (with English translation).
Office Action in Ukrainian Appln. No. a202201150, dated Feb. 10, 2025, 3 pages (with English translation).
Singaporean Search Report and Written Opinion in Singaporean Appln. 11202202090Y, mailed on Jan. 15, 2025, 14 pages (English translation).
Singaporean Search Report and Written Opinion in Singaporean Appln. 11202202092S, mailed on Jan. 13, 2025, 13 pages (English translation).
United Arab Emirates Office Action in UAE Appln. No. P6000437/2022, dated Dec. 12, 2024, 8 pages.

ANTIVIRAL PRODRUGS AND PHARMACEUTICAL COMPOSITIONS THEREOF

CROSS-REFERENCE TO RELATED APPLICATIONS

This application is a 371 of PCT/US2020/050511, filed on Sep. 11, 2020, which claims the benefit of U.S. Provisional Application Ser. No. 62/898,679, filed on Sep. 11, 2019, each of which is incorporated herein by reference in its entirety.

FIELD OF INVENTION

This invention relates to antiviral compounds and compositions useful for the treatment of acquired immunodeficiency syndrome (AIDS).

BACKGROUND OF INVENTION

4'-Ethynyl-2-fluoro-2'-deoxyadenosine (EFdA) (MK-8591) represented by Formula I:

(I)

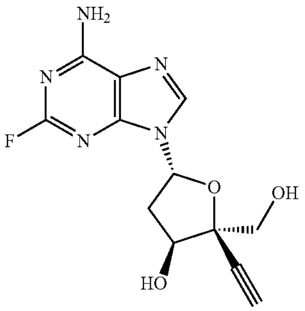

is a nucleoside analog effective as an inhibitor of nucleoside reverse transcriptase (Current Opinion in HIV and AIDS 2018, 13, 294-299) and useful as an antiretroviral in the treatment and pre-exposure prophylaxis of a HIV-1 infection. EFdA is metabolized in cells to an active triphosphate anabolite (EFdA-TP), which inhibits HIV reverse transcriptase.

EFdA, however, has a relatively high water solubility and relatively short time course of plasma concentration. As a result EFdA can provide only limited duration of viral suppression when administered to a patient for treatment of human immunodeficiency virus (HIV) infection, or for pre-exposure prophylaxis. Accordingly, there exists a need for formulations that can extend duration of viral suppression after administration. The compounds and pharmaceutical preparations of the present invention satisfy that need.

SUMMARY OF INVENTION

Antiviral compounds of the present invention are diesters of EFdA and have limited solubility in water. Whereas EFdA has an aqueous solubility of 0.877 mg/mL at physiological pH, the present diesters of EFdA have an aqueous solubility of less than 0.03 mg/mL at physiological pH, preferably less than 0.002 mg/mL. These diesters of EFdA are crystalline, are useful for providing an extended duration of suppression of HIV, and can be administered parenterally as a suspension in a pharmaceutically acceptable carrier. A preferred prophylactic dose for a human subject is in the range of about 80 mg to about 800 mg of the EFdA diester administered parenterally at about six-month intervals in a dose volume of about 0.5 to about 4 milliliters per dose. A preferred treatment dose for a human patient is in the range of about 80 mg to about 800 mg of the EFdA diester administered parenterally at about three-month intervals in a dose volume of about 0.5 to about 4 milliliters per dose Parenteral formulations containing and antiviral compound of the present invention can be dry formulations comprising the antiviral compound together with pharmaceutically acceptable excipients or stable suspensions of the antiviral compound in an aqueous or oil-based medium.

DESCRIPTION OF PREFERRED EMBODIMENTS

Extended in vivo viral suppression is achieved by diesters represented by Formula (II):

(II)

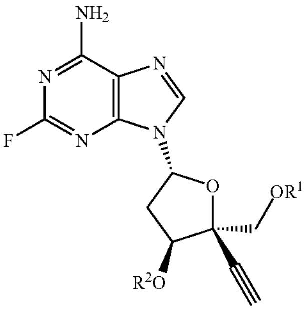

wherein $R^1$ and $R^2$ independently are —C(═O)$R^3$ and $R^3$ is a member of the group consisting of isopropyl, 3-pentyl, cyclopentyl and phenylmethyl. The foregoing diesters are prepared by reacting EFdA with the desired acid or acid anhydride and recovering the diester as a crystalline compound. The Examples below illustrate preparation of the preferred diesters.

Preparation of (2R,3S,5R)-5-(6-amino-2-fluoro-9H-purin-9-yl)-2-ethynyl-2-((isobutyryloxy)methyl)tetrahydrofuran-3-yl isobutyrate

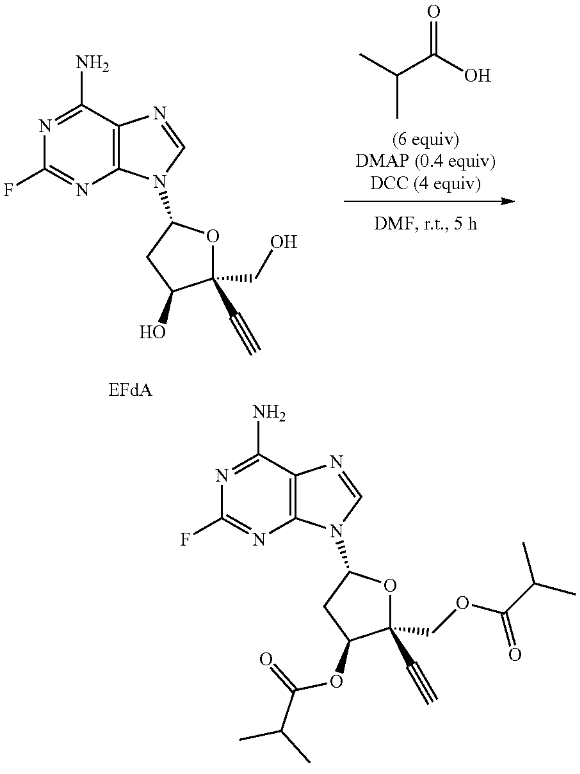

EFdA

Compound 2

To a mixture of EFdA (Compound 1) (3 g, 6.8 mmol, 1 equiv.), 4-dimethylaminopyridine (DMAP) (499 mg, 2.73 mmol, 0.4 equiv.) in anhydrous dimethyl formamide (DMF) (100 mL) isobutyric acid (8.4 g, 27.3 mmol, 6 equiv.) was added dropwise at ambient temperature. The reaction stirred for 5 h at room temperature. The reaction was monitored by LC-MS due to the occasional alkylation of $NH_2$ group observed for elongated reaction time. The reaction mixture was then filtered to remove byproduct urea. Acetonitrile was used to rinse the reaction mixture. Thereafter, the reaction mixture was washed twice with water and once with brine and then the solvent was dried, filtered and evaporated under reduced pressure. The resulting crude material was purified by silica-gel column chromatography using 60-70% ethyl acetate (EtOAc) in hexanes to obtain Compound 2 as a glassy solid. The obtained glassy solid was dispersed in minimum amount of isopropanol followed by its rotatory evaporation to obtain pure Compound 2 as a white solid (2.5 g, 85% yield). LC-MS (ESI+): m/z 434.49 $[M+H]^+$.

Figure 14:
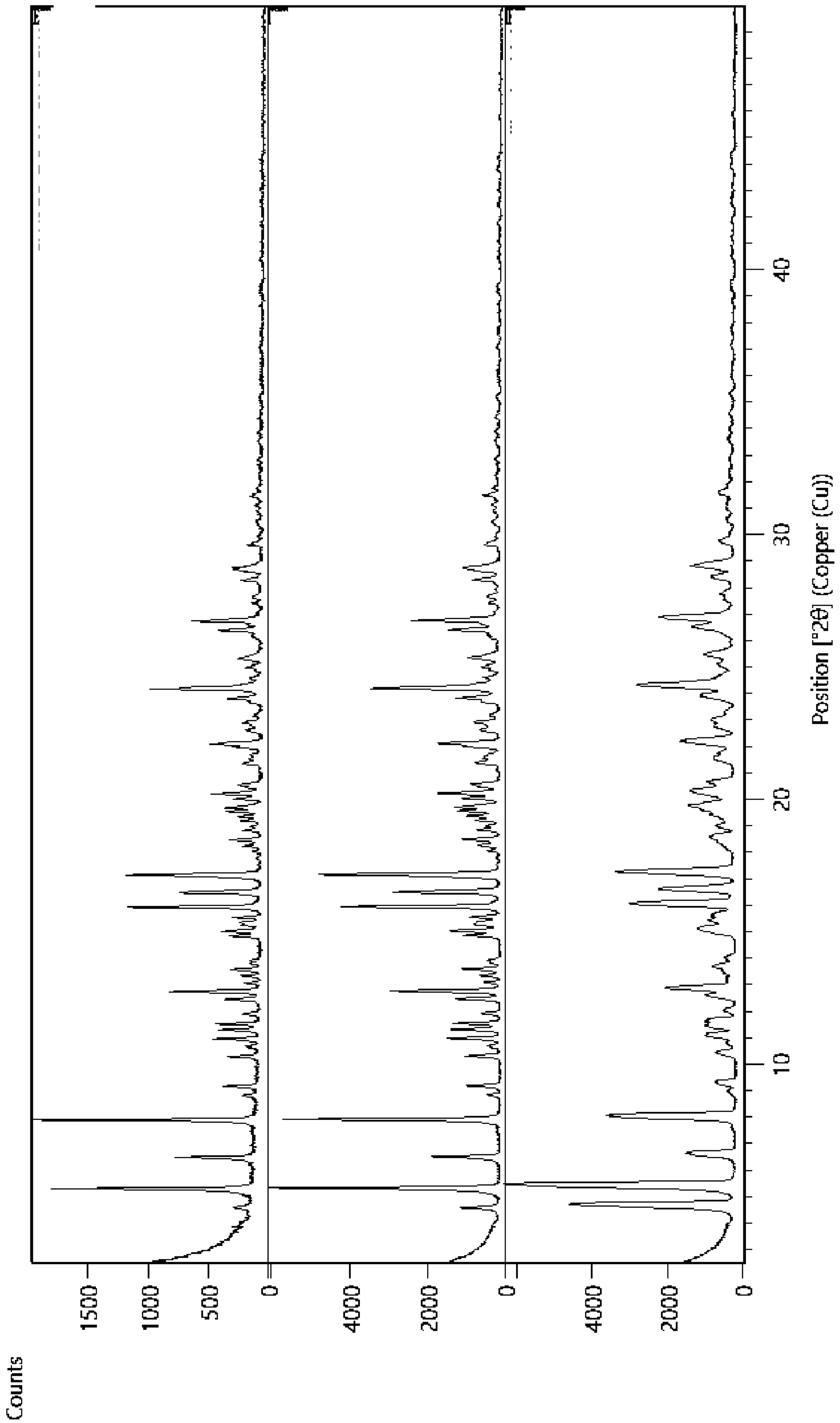
FIG. 14 shows XPRD data for Compound 2.

About 250 mg/g of Compound 2 was suspended in aqueous 0.25% CMC-Na/0.5% TWEEN-80 (26 gauge syringeability) and was subjected to stability for 2 weeks at 40° C./75% relative humidity. FIG. 14 provides XPRD data for Compound 6 from the incubated suspension, prior to incubation (bottom plot), after one week (middle plot), and after two weeks (top plot), showing that the compound retains good crystallinity in suspension.

Preparation of (2R,3S,5R)-5-(6-amino-2-fluoro-9H-purin-9-yl)-2-(((2-ethylbutanoyl)oxy)methyl)-2-ethynyltetrahydrofuran-3-yl 2-ethylbutanoate

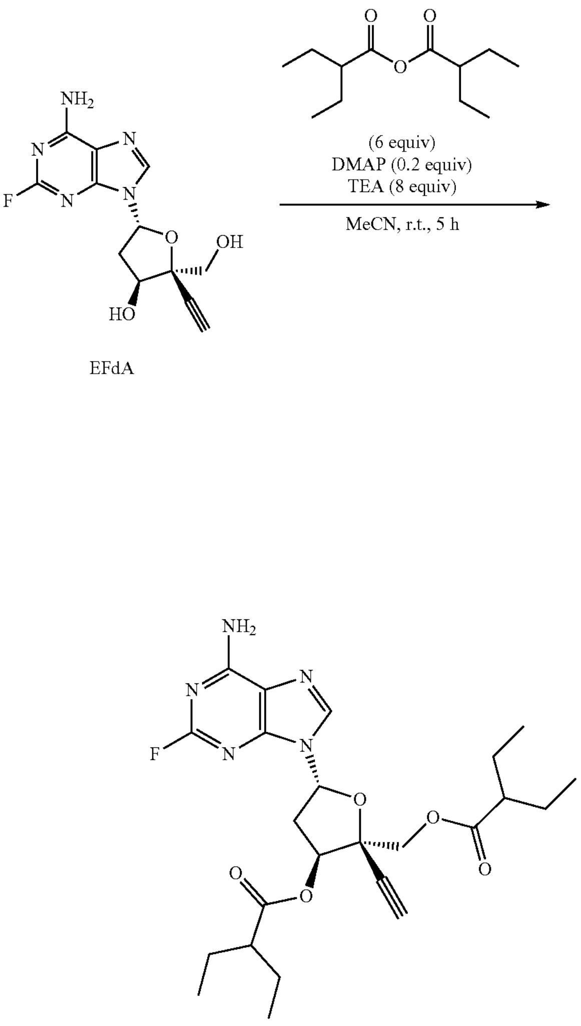

EFdA

Compound 3

To a mixture of EFdA (1 g, 3.4 mmol, 1 equiv.), 2-ethylbutanoic anhydride (4.4 g, 20.4 mmol, 6 equiv.), triethanolamine (TEA) (3.8 mL, 27.2 mmol, 8 equiv.) in anhydrous acetonitrile (MeCN) (43 mL) and cooled to 0° C. was added 4-dimethylaminopyridine (DMAP) (83 mg, 0.68 mmol, 0.2 equiv.) at 0° C. The resulting admixture was stirred for 0.5 h at 0° C. and then for 5 h at room temperature. The reaction was monitored by LC-MS due to the occasional alkylation of $NH_2$ group observed for elongated reaction time. The reaction mixture was quenched with methanol, and solvent was evaporated under reduced pressure. The resulting crude material was purified by silica-gel column chromatography using 60-70% ethyl acetate (EtOAc) in hexanes to obtain Compound 3 as a glassy solid.

The obtained glassy solid was dispersed in minimum amount of isopropanol followed by its rotatory evaporation to obtain pure Compound 3 as a white solid (1.33 g, 80% yield). LC-MS (ESI+): m/z 490.56 $[M+H]^+$.

Preparation of (2R,3S,5R)-5-(6-amino-2-fluoro-9H-purin-9-yl)-2-(((cyclopentanecarbonyl)oxy)methyl)-2-ethynyltetrahydrofuran-3-yl cyclopentanecarboxylate Compound 4

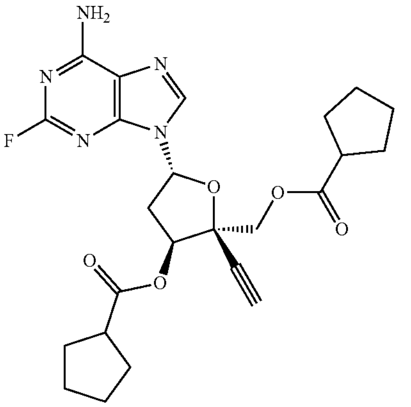

Compound 4 was prepared by using the procedure followed for the Compound 2 but using cyclopentanoic acid instead of isobutyric acid. LC-MS (ESI+): m/z 486.44 $[M+H]^+$.

Preparation of (2R,3S,5R)-5-(6-amino-2-fluoro-9H-purin-9-yl)-2-ethynyl-2-((2-phenylacetoxy)methyl) tetrahydrofuran-3-yl 2-phenylacetate

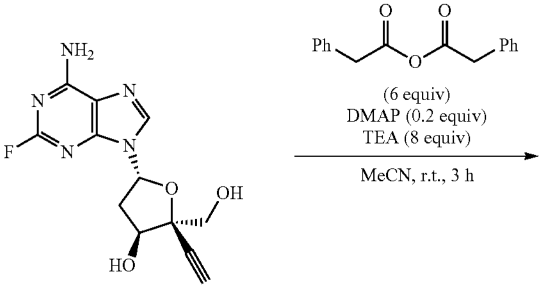

EFdA

-continued

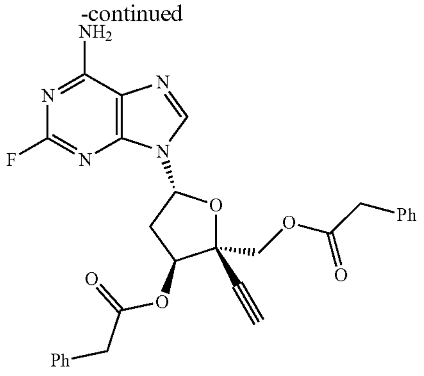

Compound 5

To a mixture of EFdA (499 mg, 1.7 mmol, 1 equiv.), 2-phenylacetic anhydride (2.6 g, 10.2 mmol, 6 equiv.), triethanolamine (TEA) (1.9 mL, 13.6 mmol, 8 equiv.) in anhydrous acetonitrile (MeCN) (22 mL) and cooled to 0° C. was added 4-dimethylaminopyridine (DMAP) (42 mg, 0.34 mmol, 0.2 equiv.) at 0° C. The reaction stirred for 0.5 h at 0° C. and then to 3 h at room temperature. The reaction is monitored by LC-MS due to the occasional alkylation of $NH_2$ group observed for elongated reaction time. The reaction mixture was quenched with methanol and solvent was evaporated under reduced pressure. The resulting crude material was purified by silica-gel column chromatography using 60-70% ethyl acetate (EtOAc) in hexanes to obtain Compound 5 as a glassy solid. The obtained glassy solid was dispersed in minimum amount of isopropanol followed by its rotatory evaporation to obtain pure Compound 5 as a white solid (694 mg, 77% yield). LC-MS (ESI+): m/z 530.52 $[M+H]^+$.

Table 1 presents compound characterization data obtained by nuclear magnetic resonance (NMR) and liquid chromatography-mass spectrometry (LC-MS).

(2R,3S,5R)-5-(6-amino-2-fluoro-9H-purin-9-yl)-2-((benzoyloxy)methyl)-2-ethynyl tetrahydrofuran-3-yl benzoate, Compound 6

Figure 15:
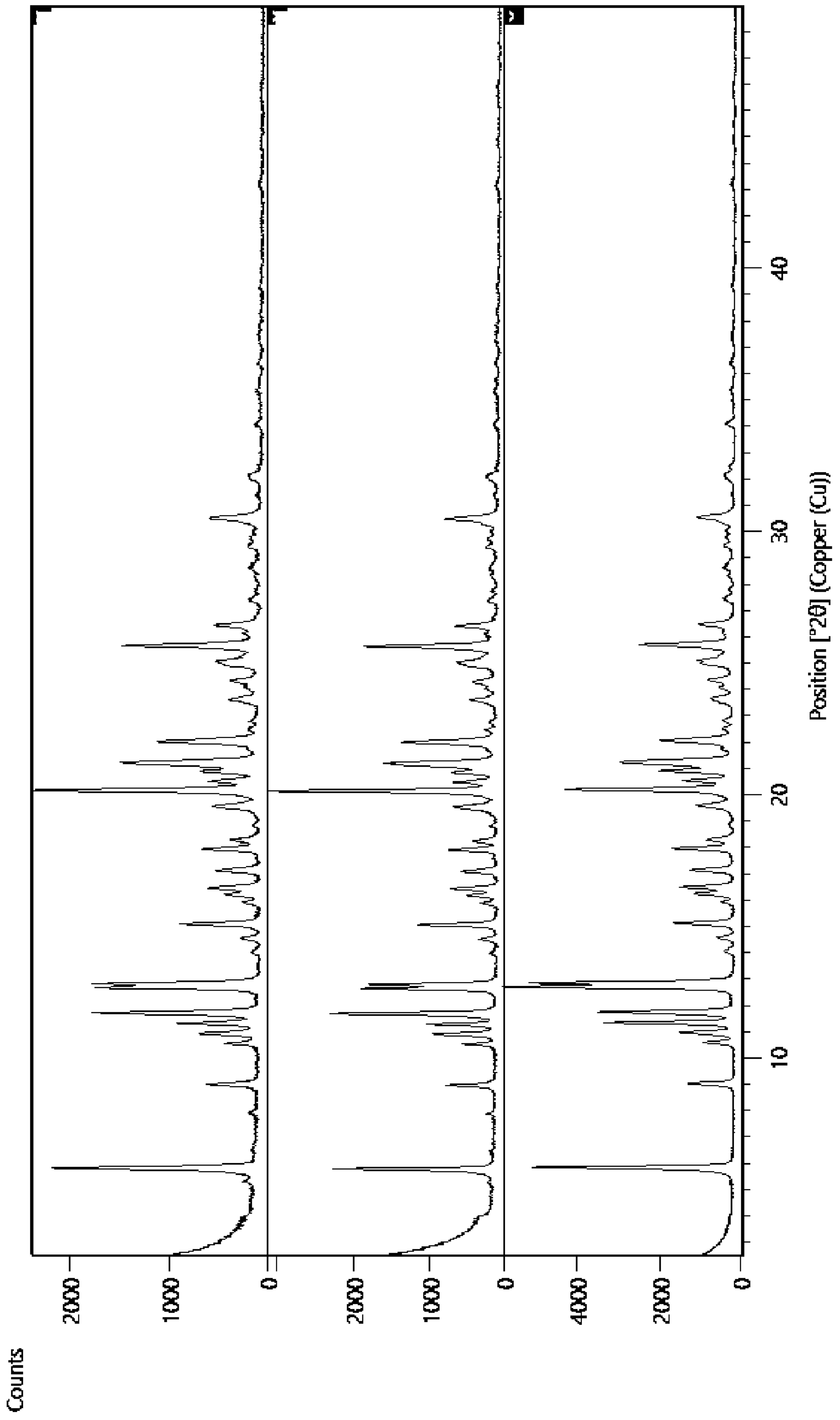
FIG. 15 shows XPRD data for Compound 6.

Compound 6 was prepared by using the procedure similar to that used for Compound 2 using 4.5 equiv of corresponding acid. LC-MS (ESI+): m/z 502.41 $[M+H]^+$. About 275 mg/g of Compound 6 was suspended in aqueous 0.25% CMC-Na/0.5% TWEEN-80 (26 gauge syringeability) and was subjected to stability for 2 weeks at 40° C./75% relative humidity. FIG. 15 provides XPRD data for Compound 6 from the incubated suspension, prior to incubation (bottom plot), after one week (middle plot), and after two weeks (top plot), showing that the compound retains good crystallinity in suspension.

TABLE 1

| Preferred Compounds | | |
|---|---|---|
| Cpd # | Structure | Characterization Data (NMR and LC-MS) |
| 2 | 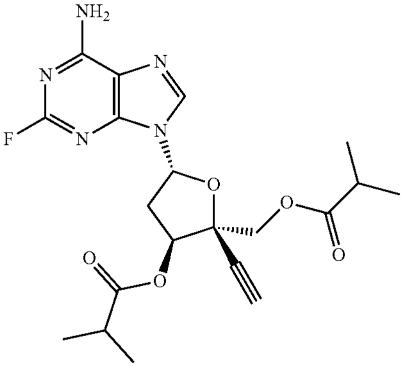 [SMILES: C#C[C@]1(COC(=O)C(C)C)O[C@@H](n2cnc3c(N)nc(F)nc32)C[C@@H]1OC(=O)C(C)C] | $^1$H NMR (400 MHz, DMSO-$d_6$) δ 8.34 (s, 1H), 7.96 (s, 1H), 7.87 (s, 1H), 6.35 (t, J = 6.6 Hz, 1H), 5.68 (t, J = 5.6 Hz, 1H), 4.40 (dd, J = 11.9, 1.5 Hz, 1H), 4.21 (d, J = 10.4 Hz, 1H), 3.81 (s, 1H), 3.18 (dt, J = 13.6, 6.8 Hz, 1H), 2.69-2.57 (m, 2H), 1.2-1.1 (m, 6H), 1.08-0.98 (m, 6H). MS-ESI: m/z 434.49 observed $(M + H)^+$ Anal calcd for $C_{20}H_{24}F_5O_5$: C, 55.42; H, 5.58; N, 16.16. Found: C, 55.48; H, 5.73; N, 15.94 Aqueous solubility (pH 7.4): 0.028 mg/mL |
| 3 | 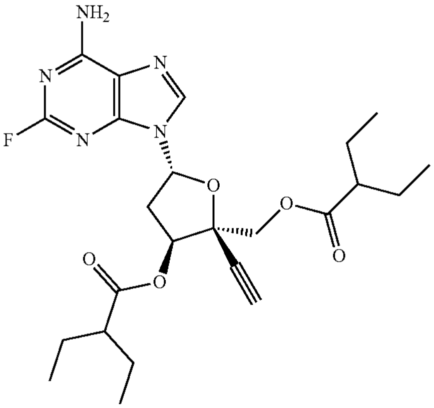 [SMILES: C#C[C@]1(COC(=O)C(CC)CC)O[C@@H](n2cnc3c(N)nc(F)nc32)C[C@@H]1OC(=O)C(CC)CC] | $^1$H NMR (400 MHz, DMSO-$d_6$) δ 8.35 (s, 1H), 7.91 (d, J = 39.8 Hz, 2H), 6.35 (t, J = 6.8 Hz, 1H), 5.73 (t, J = 6.5 Hz, 1H), 4.38 (dd, J = 11.8, 2.5 Hz, 1H), 4.24 (dd, J = 11.7, 2.5 Hz, 1H), 3.81 (s, 1H), 3.20 (dt, J = 13.5, 6.8 Hz, 1H), 2.61 (dt, J = 13.2, 6.6 Hz, 1H), 3.39 (ddd, J = 8.3, 5.6, 2.6 Hz, 1H), 2.13 (tt, J = 8.9, 5.9 Hz, 1H), 1.72-1.31 (m, 8H), 0.88 (td, J = 7.5, 2.3 Hz, 6H), 0.80-0.66 (m, 6H). MS-ESI: m/z 490.56 observed $(M + H)^+$ Aqueous solubility (pH 7.4): <0.002 mg/mL |
| 4 | 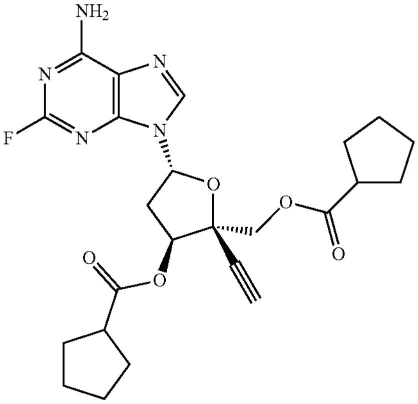 [SMILES: C#C[C@]1(COC(=O)C2CCCC2)O[C@@H](n2cnc3c(N)nc(F)nc32)C[C@@H]1OC(=O)C1CCCC1] | $^1$H NMR (400 MHz, DMSO-$d_6$) δ 8.34 (s, 1H), 7.92 (d, J = 36.1 Hz, 2H), 6.34 (t, J = 6.8 Hz, 1H), 5.68 (t, J = 6.2 Hz, 1H), 4.39 (dt, J = 11.6, 1.8 Hz, 1H), 4.21 (dd, J = 11.6, 2.4 Hz, 1H), 3.81 (s, 1H), 3.18 (dt, J = 13.9, 6.9 Hz, 1H), 2.90-2.78 (m, 1H), 2.74-2.57 (m, 2H), 1.93-1.44 (m, 16H). MS-ESI: m/z 486.44 observed $(M + H)^+$ Aqueous solubility (pH 7.4): <0.001 mg/mL |
| 5 | 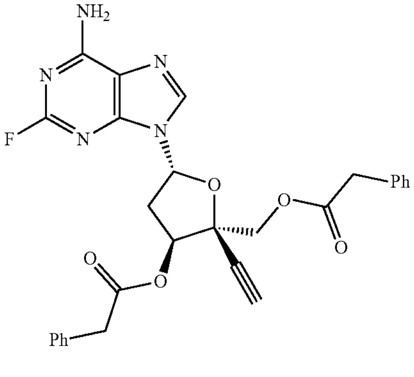 [SMILES: C#C[C@]1(COC(=O)Cc2ccccc2)O[C@@H](n2cnc3c(N)nc(F)nc32)C[C@@H]1OC(=O)Cc1ccccc1] | $^1$H NMR (400 MHz, DMSO-$d_6$) δ 8.31 (s, 1H), 7.93 (d, J = 37.3 Hz, 2H), 7.39-7.12 (m, 10H), 6.35 (t, J = 6.7 Hz, 1H), 5.71 (t, J = 6.0 Hz, 1H), 4.41 (d, J = 11.7 Hz, 1H), 4.25 (d, J = 11.3 Hz, 1H), 3.88-3.71 (m, 3H), 3.63 (q, J = 15.8 Hz, 2H), 3.11 (dt, J = 14.0, 7.0 Hz, 1H), 2.63 (dt, J = 12.5, 6.4 Hz, 1H). MS-ESI: m/z 530.2 observed $(M + H)^+$ Aqueous solubility (pH 7.4): <0.002 mg/mL |

TABLE 1-continued

| Preferred Compounds | | |
|---|---|---|
| Cpd # | Structure | Characterization Data (NMR and LC-MS) |
| 6 | 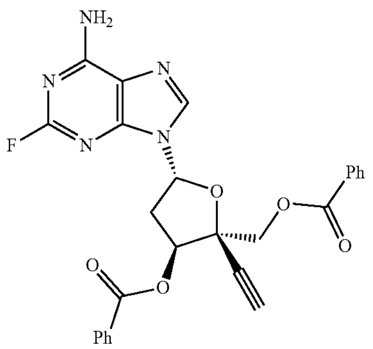 [SMILES: C#C[C@]1(COC(=O)c2ccccc2)O[C@@H](n2cnc3c(N)nc(F)nc32)C[C@@H]1OC(=O)c1ccccc1] | $^1$H NMR (400 MHz, DMSO-$d_6$) δ 8.38 (s, 1H), 8.09 (dt, J = 8.6, 1.4 Hz, 2H), 8.02-7.83 (m, 4H), 7.76-7.68 (m, 1H), 7.66 (td, J = 7.4, 1.5 Hz, 1H), 7.59 (td, J = 7.6, 7.1, 1.7 Hz, 2H), 7.53-7.44 (m, 2H), 6.54 (t, J = 6.8 Hz, 1H), 6.16-6.08 (m, 1H), 4.72 (d, J = 11.6 Hz, 1H), 4.59 (d, J = 11.5 Hz, 1H), 3.84 (s, 1H), 3.41-3.32 (m, 1H), 2.85 (dt, J = 13.4, 6.3 Hz, 1H). MS-ESI: m/z 502.41 observed $(M + H)^+$ Aqueous solubility (pH 7.4): <0.002 mg/mL |

The foregoing discussion and the Examples are illustrative, and are not to be taken as limiting. Still other variants within the spirit landscape of this invention are possible and will readily present themselves to those skilled in the art.

Synthesis of Stable Crystalline Forms

Example 1

Compound 2 (~200 mg) was completely dissolved in minimum quantity of acetone with stirring. This was followed by slow evaporation of the solvents at ambient temperature. This resulted in a recrystallized sample as a white powder. Other solvents including ethyl acetate, methanol and tetrahydrofuran can also be used.

General Examples for the formulation of Compounds of the Invention

All formulation protocols generated a stable aqueous suspension with 26-gauge syringeability.

EFdA Formulation

EFdA was ground and sieved through a #80 sieve. A solution of preformed 0.25% sodium carboxymethyl cellulose (Sodium CMC)& 0.1% polyoxyethylene (20) sorbitan monooleate (TWEEN-80) was added to about 300 mg of EFdA (Compound 1) to provide a suspension of about 1 gram (300 mg of 1+~700 mg of polymer solution) of the final formulation (about 300 mg/g). The suspension was then bath sonicated for 10 min in an ice bath. The density of formulation of was 1.064 g/mL and provided a 319.2 mg/mL concentration of EFdA.

Example 2

Recrystallized Compound 2 was ground and sieved through No. 80 sieve U.S. Standard Sieve Series, for Wire Cloth Screens (nominal sieve opening 0.180 mm). 250 mg of Compound 2 was taken in suitable container and a solution of preformed 0.25% Sodium Carboxymethylcellulose (CMC) and 0.1% TWEEN-80 was added to obtain 1 gram (250 mg of Compound 2+~750 mg of polymer solution) of the final formulation (~250 mg/g). The suspension was then probe sonicated for 5 min in an ice bath (Sonication time: 5 min; Pulse Amplitude: 20; Pulse on Time: 30 sec; Pulse off time: 20 sec).

Example 3

Compound 3 was ground and sieved through No. 80 sieves U.S. Standard Sieve Series for Wire Cloth Screens (nominal sieve opening 0.180 mm). 250 mg of Compound 3 was taken in suitable container and a solution of preformed 0.25% Sodium CMC and 0.5% TWEEN-80 was added to obtain 1 gram (250 mg of Compound 3+~750 mg of polymer solution) of the final suspension (~250 mg/g). The suspension was then probe sonicated for 5 min in an ice bath (Sonication time: 5 min; Pulse Amplitude: 20; Pulse on Time: 30 sec; Pulse off time: 20 sec). The density of the suspension was of is 1.004 g/mL. The above Suspension contained 250.88 mg/mL of Compound 3 (~150 mg/mL of EFdA).

Example 4

Compound 5 was ground and sieved through No. 80 sieve U.S. Standard Sieve Series for Wire Cloth Screens (nominal sieve opening 0.180 mm). 200 mg of Compound 5 was placed in a suitable container and a solution of preformed 0.25% Sodium CMC and 0.5% TWEEN-80 was added to obtain 1 gram (200 mg of Compound 5+~800 mg of polymer solution) of the final suspension (~200 mg/g). The suspension was then probe sonicated for 5 min in an ice bath (Sonication time: 5 min; Pulse Amplitude: 20; Pulse on Time: 30 sec; Pulse off time: 20 sec). The density of the suspension was 1.047 g/mL. The above suspension contained 209.4 mg/mL of Compound 5 (~115.97 mg/mL of EFdA).

Pharmacokinetic (PK) Studies

- Animals: Animals (Male SD rats ~200-250 g and Male rhesus macaques ~2-3 kg) were obtained from an approved vendor (SLAC Laboratory Animal Co. Ltd., Shanghai, China and/or Topgene Biotechnology, Wuhan city, Hubei Province, China).
- Acclimation/Quarantine: Following arrival, animals were assessed as to their general health by a member of the veterinary staff or other authorized personnel. Animals were acclimated for at least 3 days before being placed on study.

Animal Husbandry: Animals were group housed during acclimation and individually housed during the study. The animal room environment will be controlled (target conditions: temperature 18 to 26° C., relative humidity 30 to 70%, 12 hours artificial light and 12 hours dark). Temperature and relative humidity were monitored daily.

Animal Cannulation: No

Animals were fasted at least 12 hours prior to the administration. All animals had access to Certified Rodent and non-Rodent Diet (Catalog #M01-F, SLAC Laboratory Animal Cl. Ltd., Shanghai, China) ad libitum 4 hours post dosing.

Water was autoclaved before provided to the animals ad libitum. Periodic analyses of the water was performed and the results archived. There were no known contaminants in the diet or water that, at the levels of detection, were expected to interfere with the purpose, conduct or outcome of the study.

1. Dose Formulation

SC Formulation: Suspensions were prepared on the day of dosing according to the procedure described in Examples 2-5 above, and Tables 2-4. Animals were dosed within four hours of suspension preparation. Two 20 μL aliquots of each prepared suspension were transferred into 1.5 mL of polypropylene microcentrifuge tubes and dose validation was run by LC/UV or LC-MS/MS.

2. Dose Administration

The suspensions were administered via subcutaneous injection (SC) following facility standard operations procedures (SOPs).

3. Sample Collection

Approximately 200 μL blood was collected from saphenous vein at each time point for rats and 0.5 mL for rhesus macaques. All blood samples were transferred into microcentrifuge tubes containing 4 μL of $K_2EDTA$ (0.5M) as anti-coagulant and placed on wet ice until processed for plasma.

4. Blood/Plasma Processing

Blood: Blood samples were processed for plasma by centrifugation at approximately 4° C., 3000 g 15 min within half an hour of collection. Plasma samples was stored in polypropylene tubes, quick frozen over dry ice and kept at −70±10° C. until LC/MS/MS analysis.

5. Sample Analysis

Dose Concentration Verification

Aliquots of the prepared suspension were collected in the middle position of each suspension in duplicate.

The concentration of the active ingredient in each aliquot was determined by the LC/UV or LC/MS/MS method Bioanalytical Method and Sample Analysis LC-MS/MS methods for the quantitative determination of active ingredient (test compound) in corresponding biological matrix was developed under non-GLP compliance.

A calibration curve with 8 non-zero calibration standards was applied for the method including lower limit of quantitation (LLOQ).

A set of quality control (QC) samples consisting of low, middle, and high concentration was applied for the method.

The study sample analysis will be performed concurrently with a set of calibration standards and two sets of QC samples using the LC-MS/MS method (If sample numbers were more than 48, then two calibration curves with 2 sets of QC samples were applied).

Acceptance criteria:

Linearity: a minimum of 6 calibration standards was back calculated to within ±20% of their nominal values in plasma Accuracy: A minimum of 4 out of 6 QC samples was back calculated to within +20% of their nominal values in plasma.

Specificity: The mean calculated concentration in the single blank matrix should be 0.5 times the LLOQ.

Sensitivity: the LLOQ will target 1~3 ng/mL.

Carryover: the mean calculated carry-over concentration in the single blank matrix immediately after the highest standard injection should be LLOQ. If the carryover couldn't meet the criteria, then the percent of carryover should be estimated following in-house bioanalytical SOP.

6. Data Analysis

Plasma concentration versus time data was analyzed by non-compartmental approaches using the Phoenix WinNonlin 6.3 software program. $C_{max}$, $T_{max}$, $T_{1/2}$, $AUC_{(0-t)}$, $AUC_{(0-inf)}$, $MRT_{(0-t)}$, $MRT_{(0-inf)}$, % F and graphs of plasma concentration versus time profile were generated.

Example 5

Several prodrugs including EFdA (1) as a control were subjected to a single dose rat PK studies via subcutaneous route of administration. All animals were injected with equivalent doses of 10 mg/kg and concentration of 4 mg/mL of EFdA as an aqueous suspension in 0.5% CMC-Na and 0.5% TWEEN-80. While similar exposure was observed, all compounds 2, 3 and 5 exhibited plasma levels of EFdA above lower limit of quantitation (LLOQ) for more than a week with Cmax much lower than for EFdA.

Figure 1:
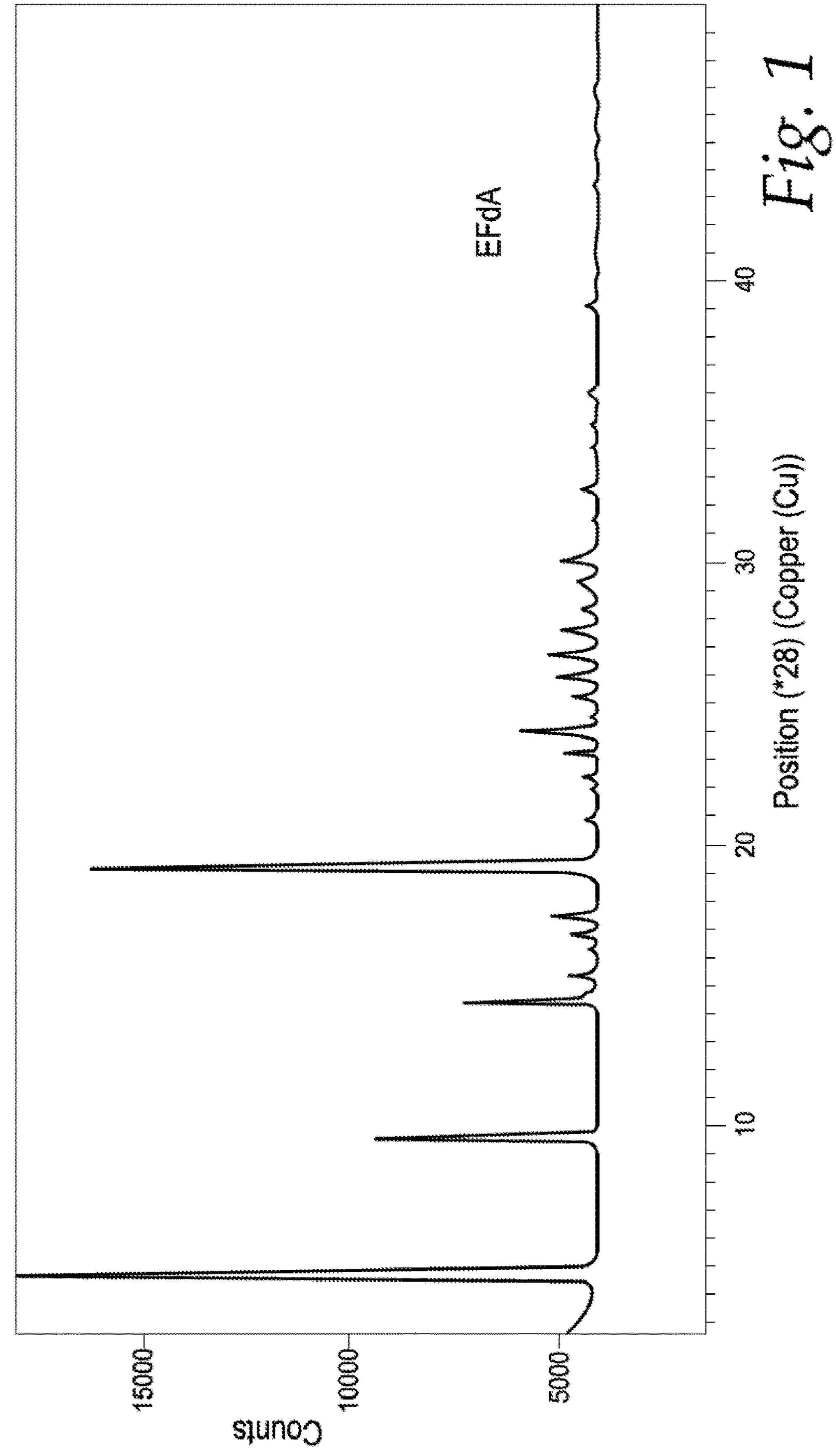
FIG. 1 shows an X-ray Powder Diffractogram (XPRD) of EFdA.
Figure 2:
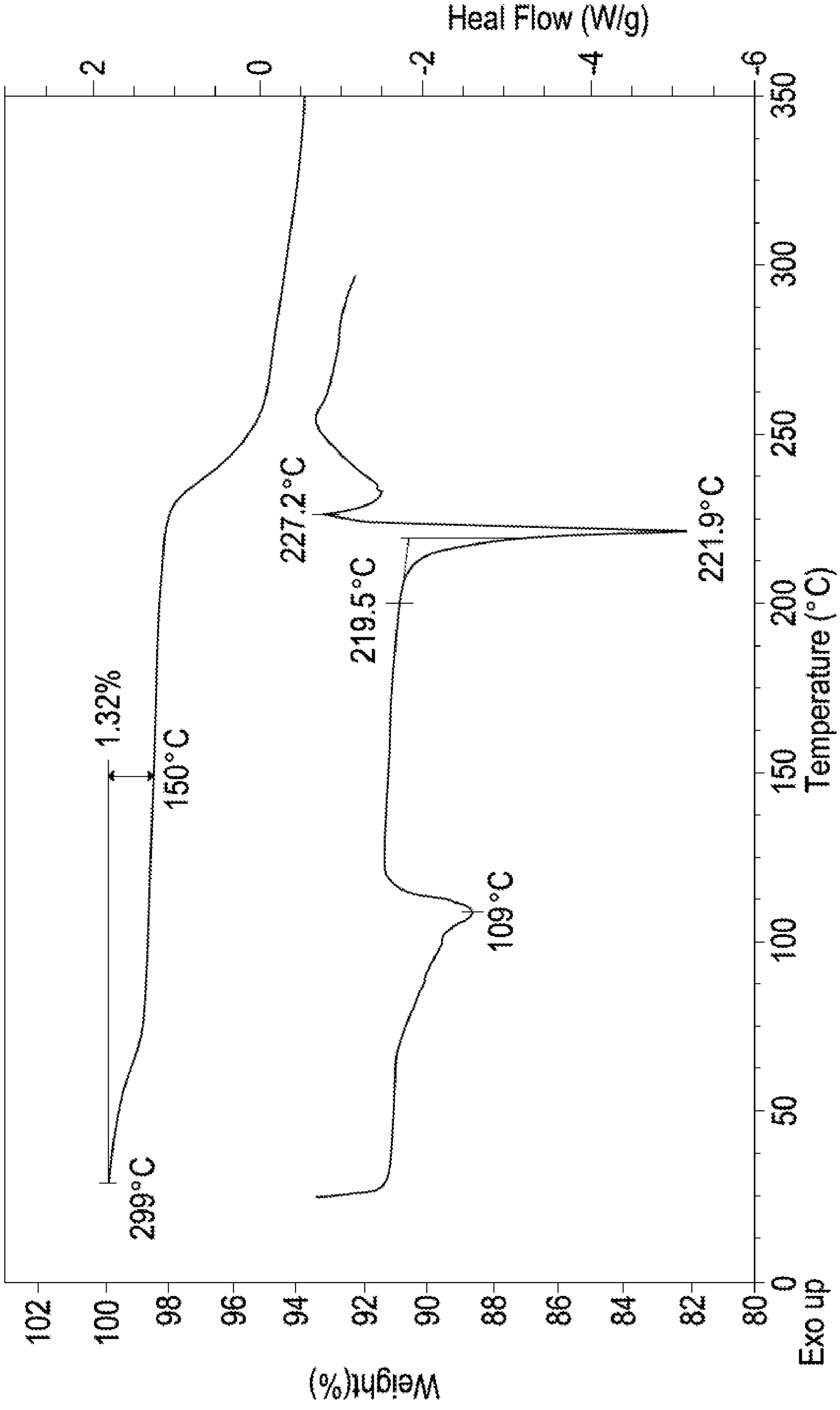
FIG. 2 shows data provided by Differential Scanning Calorimetry (DSC) and Thermo-Gravimetric Analysis (TGA) of EFdA.
Figure 3:
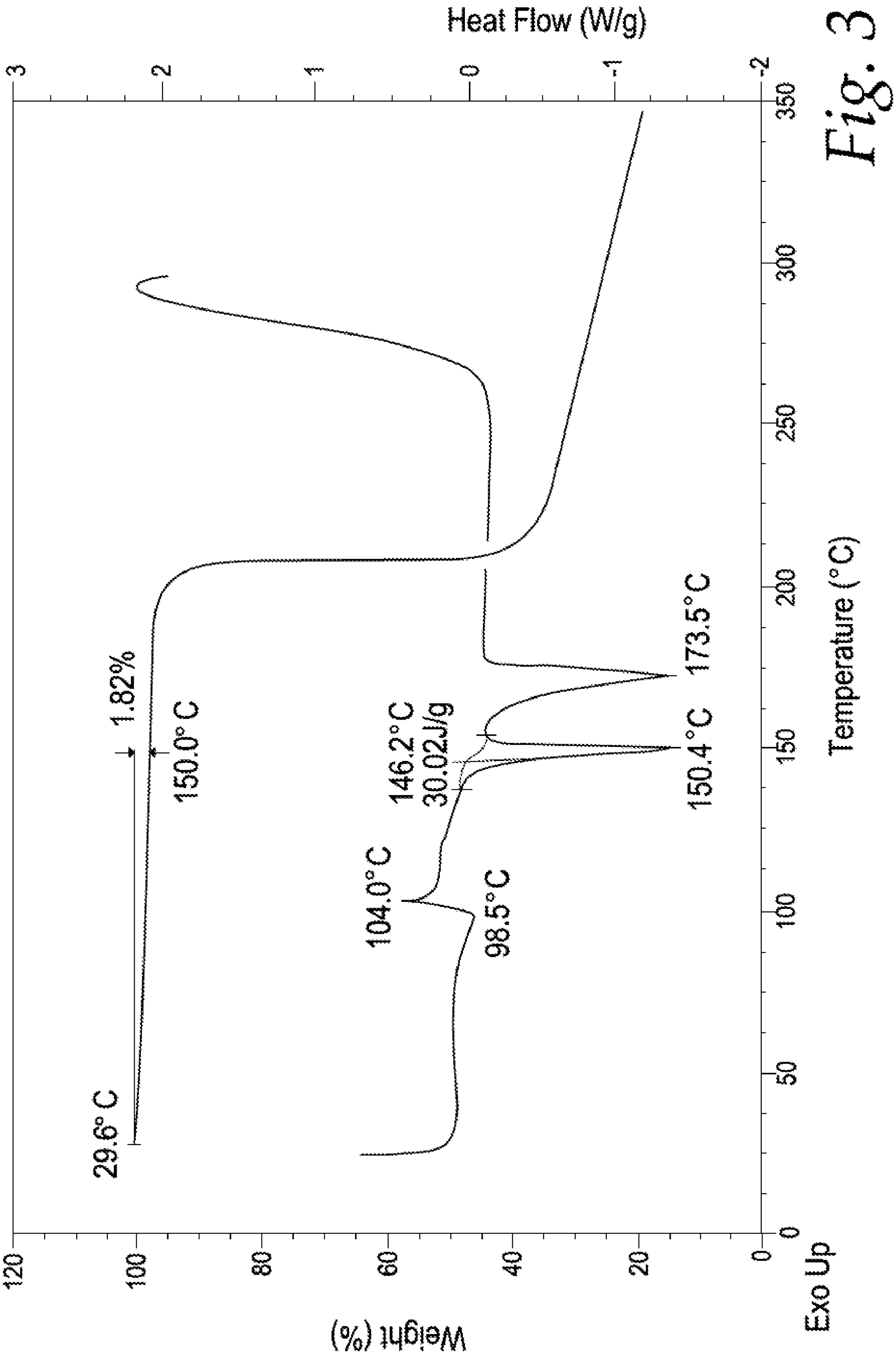
FIG. 3 shows DSC and TGA data for Compound 2.
Figure 4:
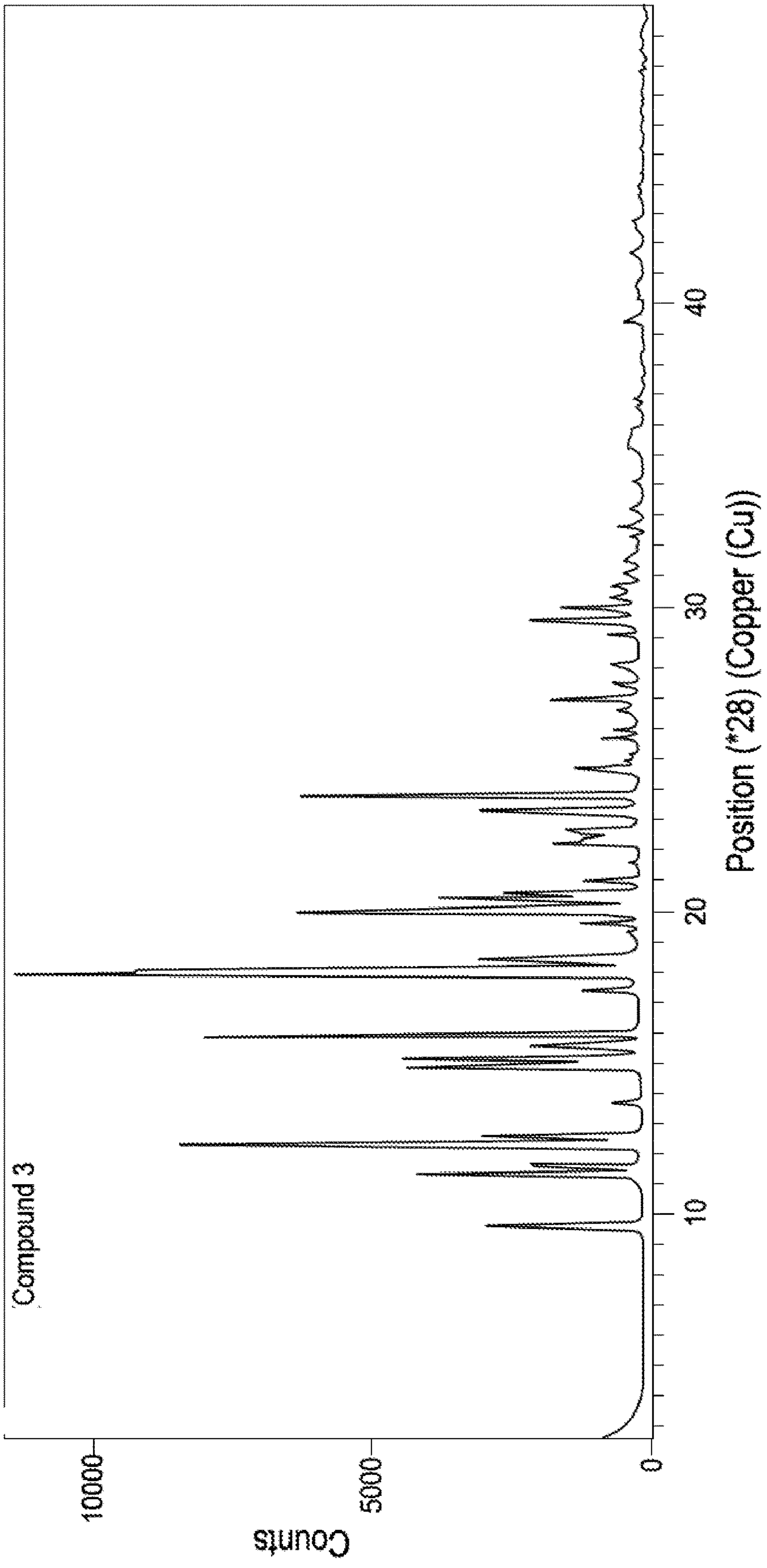
FIG. 4 shows XPRD data for Compound 3.
Figure 5:
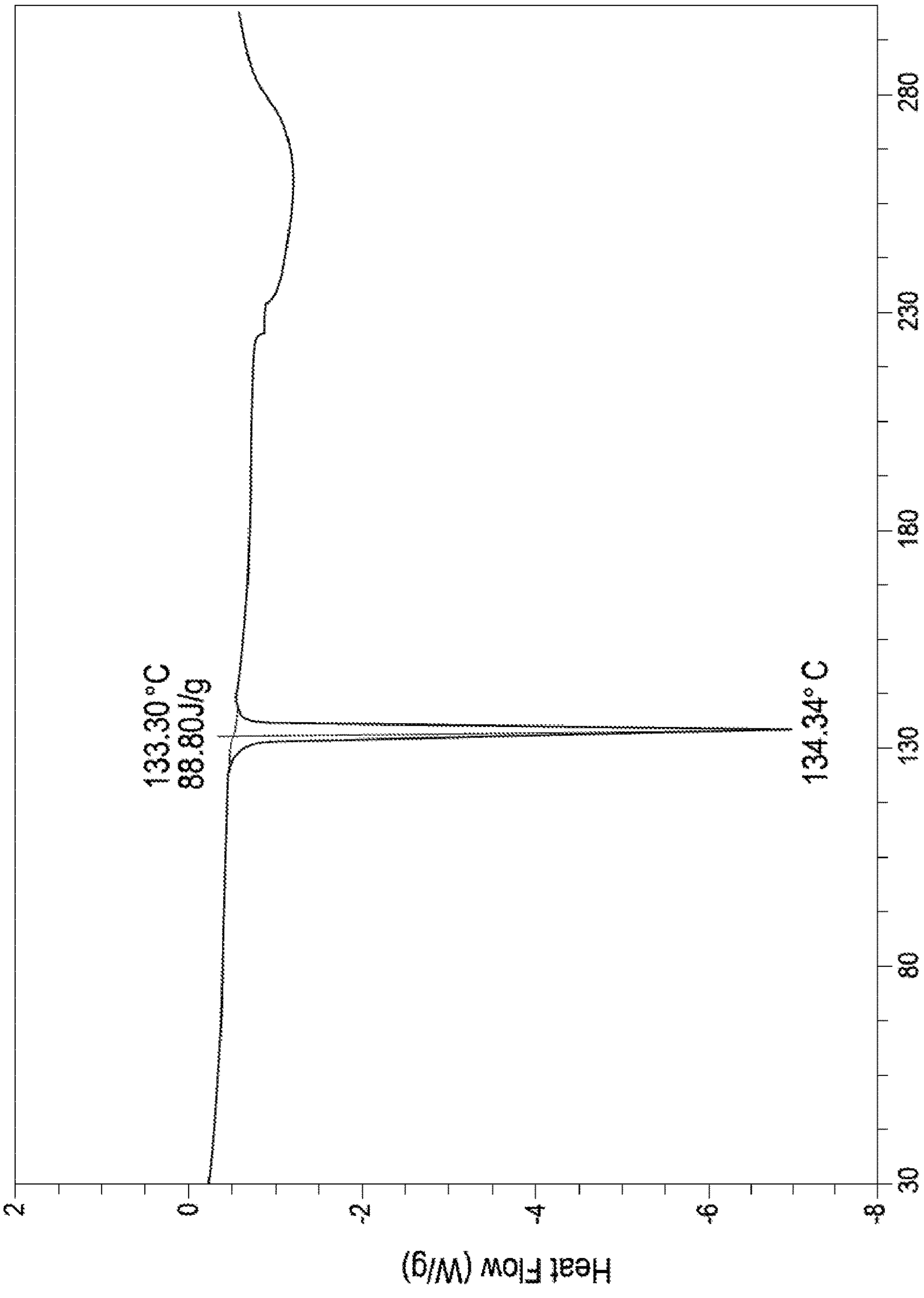
FIG. 5 shows DSC data for Compound 3.
Figure 6:
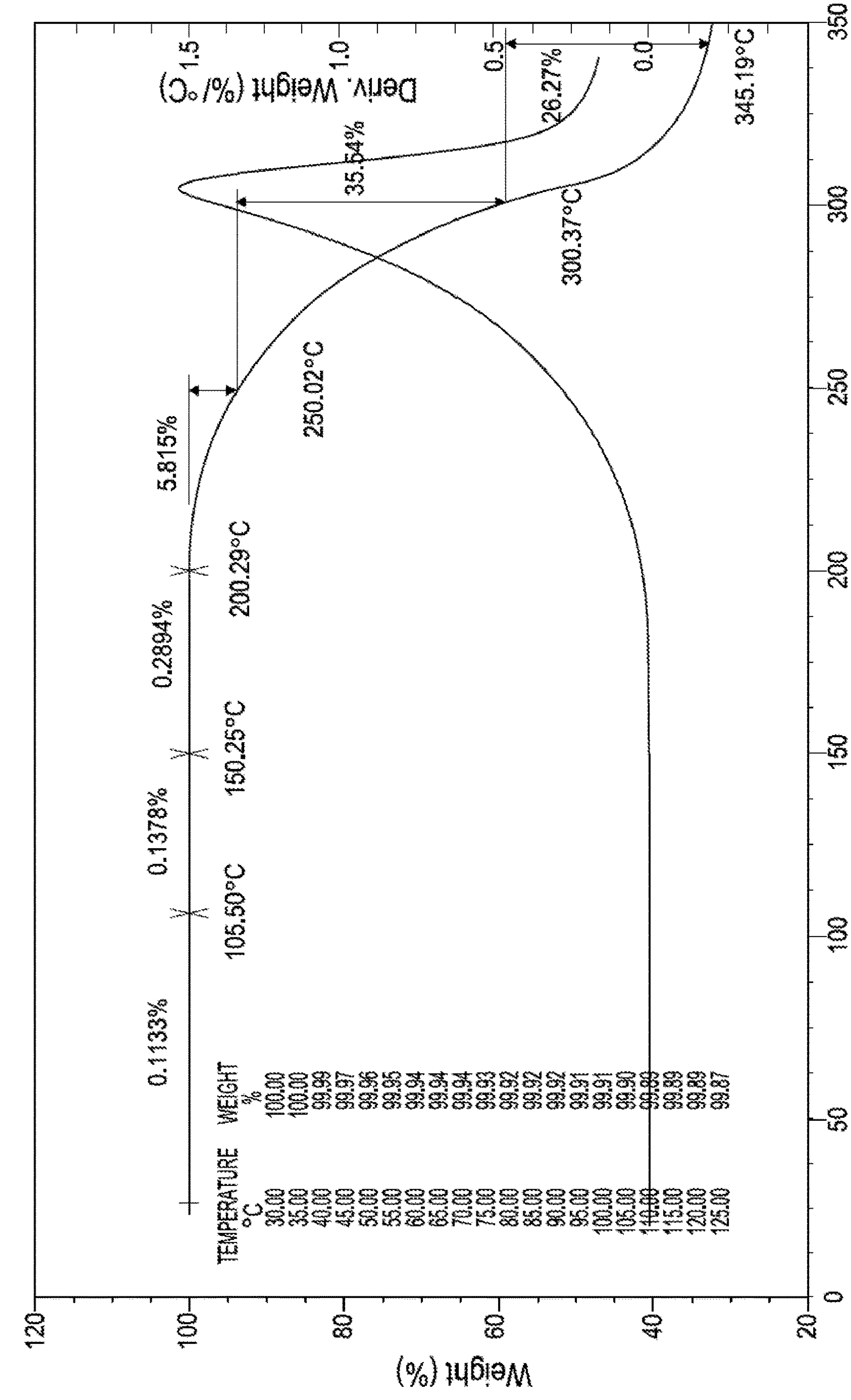
FIG. 6 shows TGA data for Compound 3.
Figure 7:
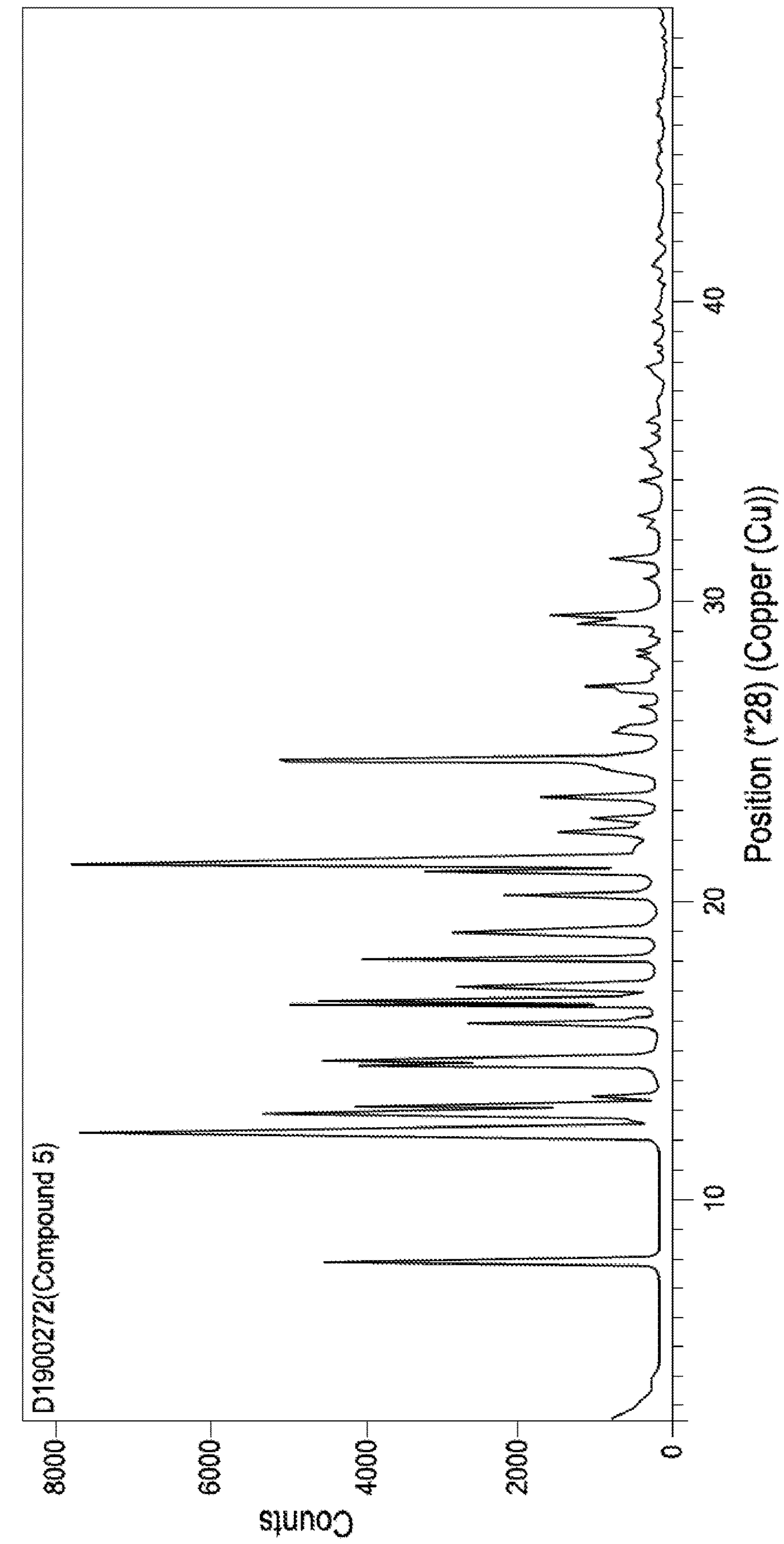
FIG. 7 shows XPRD data for Compound 5.
Figure 8:
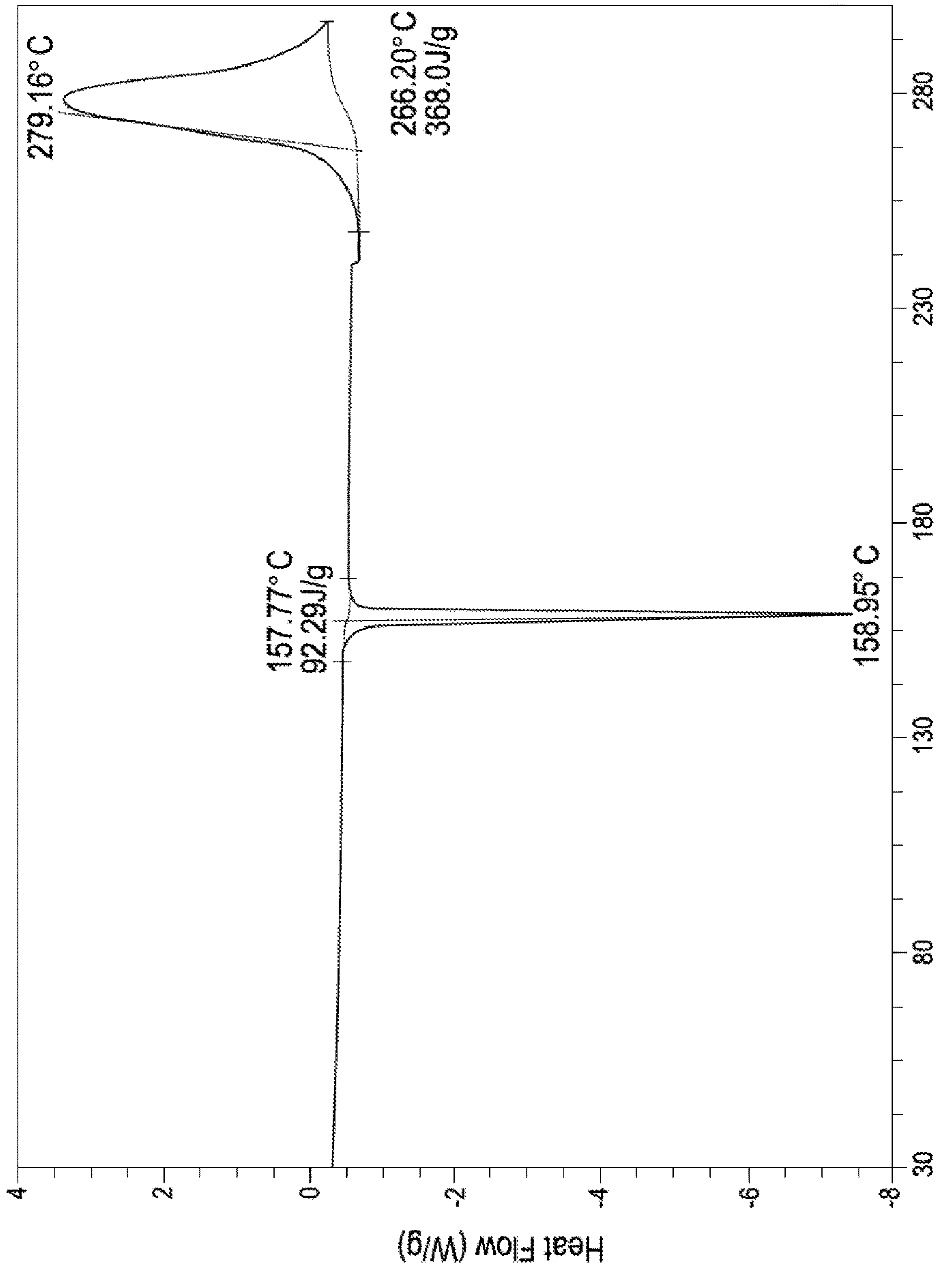
FIG. 8 shows DSC data for Compound 5.
Figure 9:
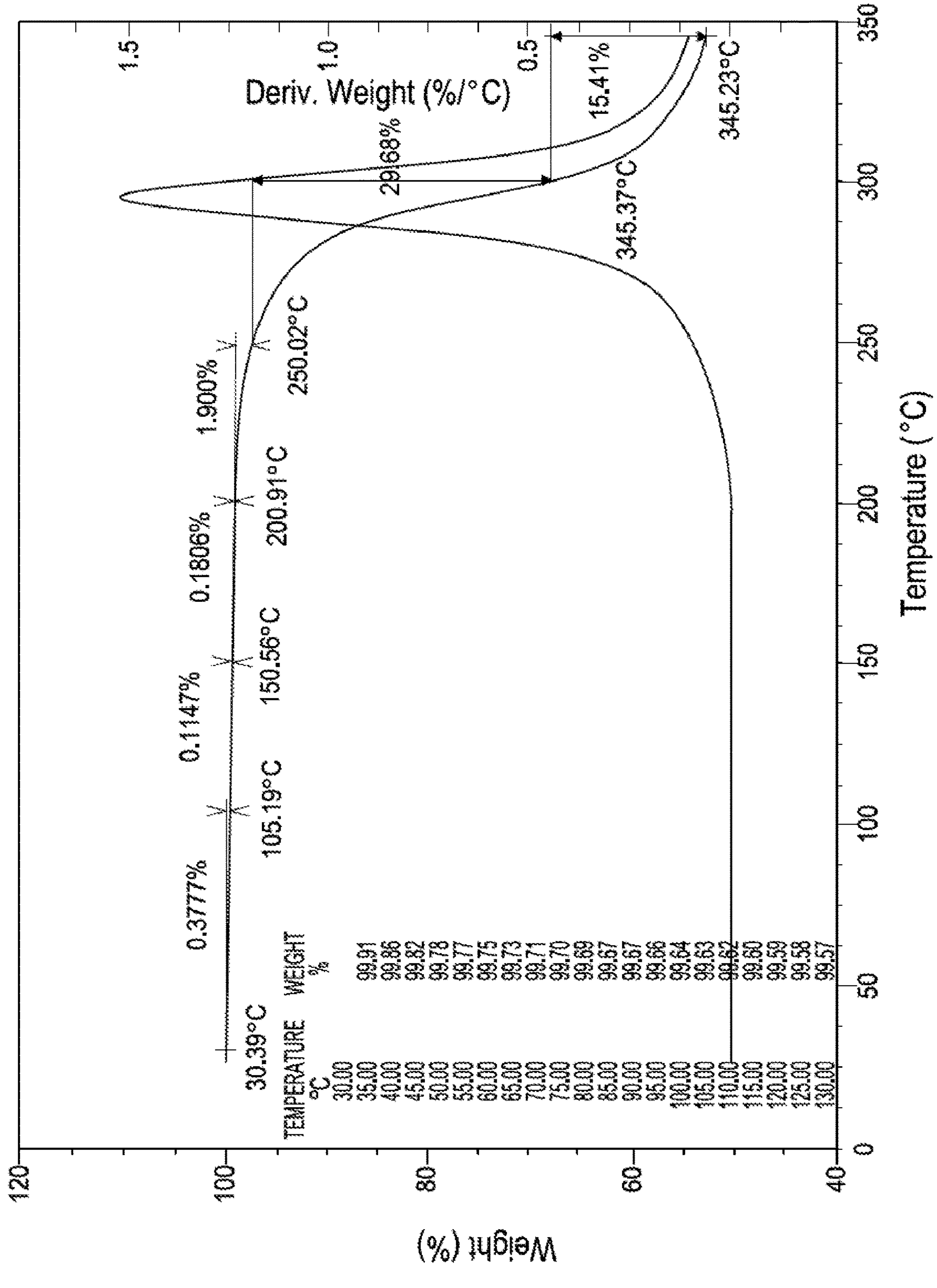
FIG. 9 shows TGA data for Compound 5.
Figure 10:
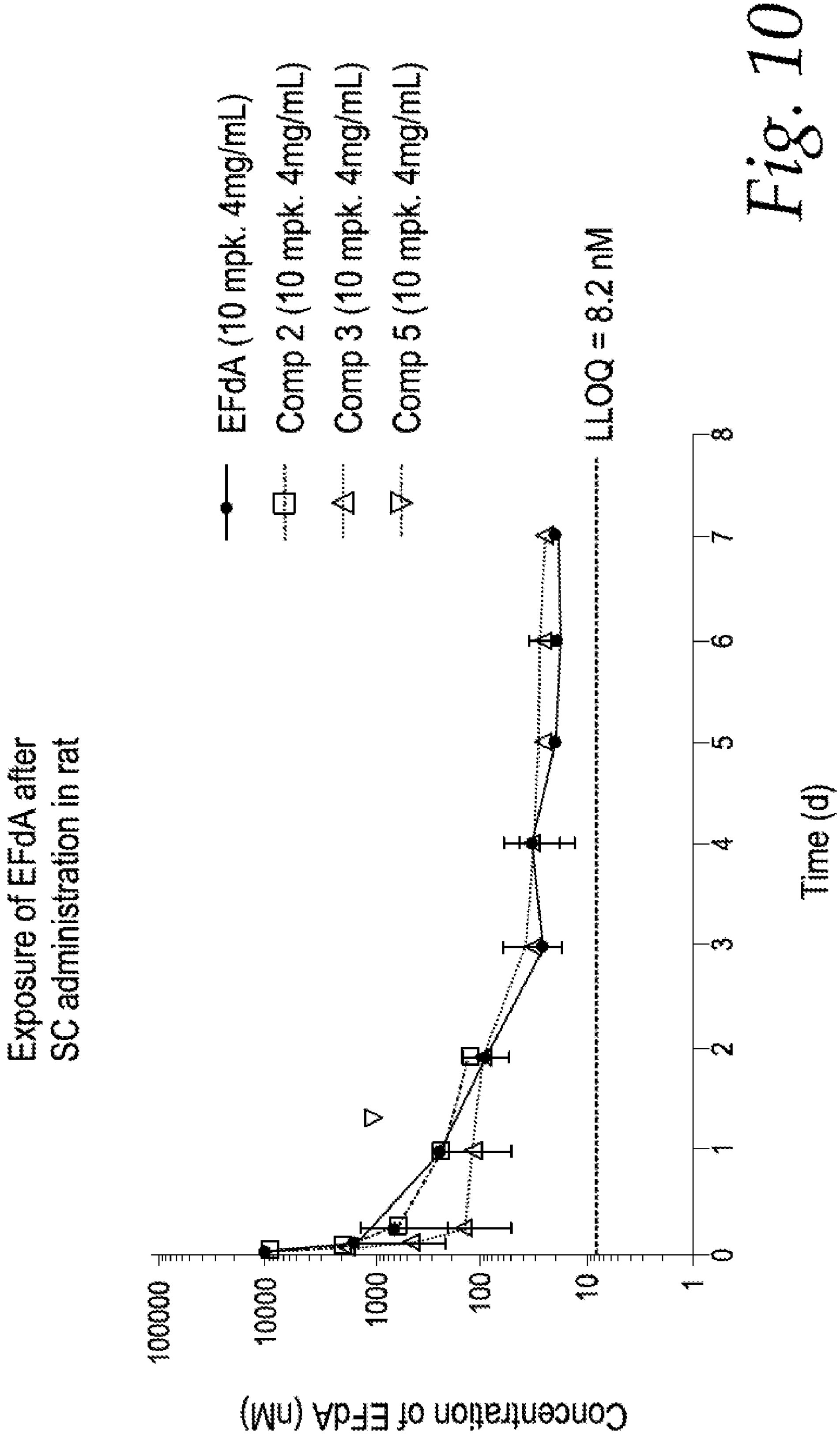
FIG. 10 shows in graphic form the data provided in Table 2.

Table 2 shows the rat PK data for Compounds 1, 2, 3 and 5 following subcutaneous (SC) administration at 10 mg/kg equivalent dose of EFdA. The data in graphic form are shown in FIG. 10.

TABLE 2

SC Rat PK: EFdA Levels for EFdA, Compounds 1,2, 3 and 5

| | SC Comp 1 (EFdA) | SC Comp 2 | SC Comp 3 | SC Comp 5 |
|---|---|---|---|---|
| Dose of EFdA (mg/kg) | 10 | 10 | 10 | 10 |
| Concentration of EFdA (mg/kg) | 4 | 4 | 4 | 4 |
| Excipients | 0.5% CMC-Na/0.5% TWEEN-80 | | | |
| $T_{1/2}$ (h) | 1.3 ± 0.2 | 17 ± 4 | NA | 12 ± 4 |
| $MRT_{0-last}$ (h) | 1.6 ± 0.1 | 12 ± 1.2 | 20 ± 4 | 13 ± 3 |
| $T_{max}$ (h) | 0.5 | 2 ± 1.1 | 4 ± 2.3 | 7 ± 0 |
| $C_{max}$ (nM) | 11,548 ± 3,173 | 1,795 ± 337 | 287 ± 177 | 968 ± 374 |
| $AUC_{0-last}$ (nM*h) | 22,528 ± 1,680 | 19,771 ± 1,219 | 6,475 ± 2,909 | 18,516 ± 4,409 |
| $AUC_{0-inf}$ (nM*h) | 23,235 ± 2,000 | 22,745 ± 748 | NA | 19,993 ± 3,525 |

Example 6

After optimization, SC rat PK studies were performed again with high equivalent dose of 100 mg/kg at equivalent concentration of 120 mg/mL for Compound 3, 116 mg/mL for Compound 5, and 319 mg/mL of EFdA, respectively. Compound 3 provided a delayed and 100-fold lower $C_{max}$ than EFdA. Enhanced half life and mean residence life were also observed, making Compound 3 and Compound 5 suitable for prophylaxis.

Figure 11:
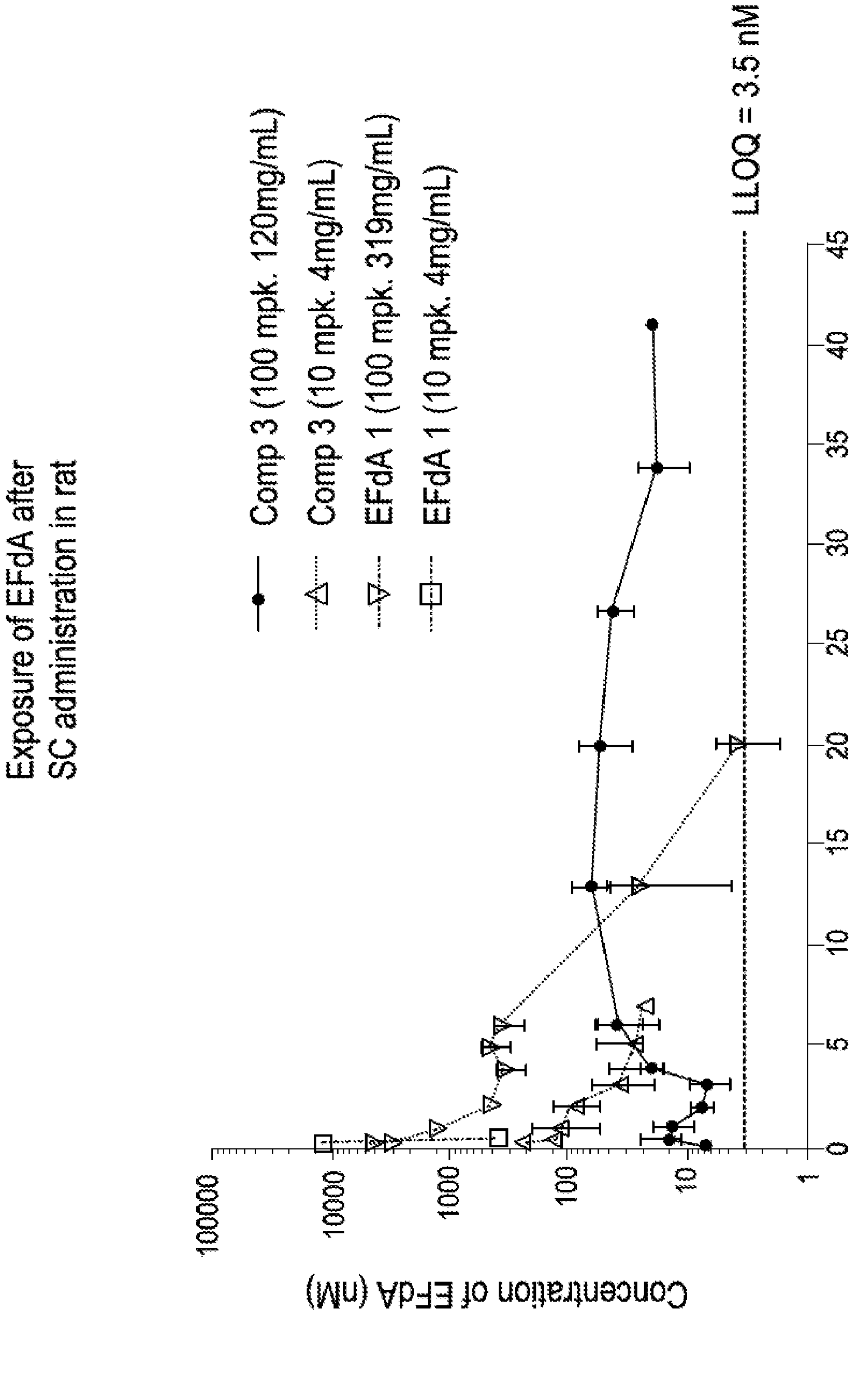
FIG. 11 shows in graphic form the data provided in Table 3.

Table 3A and Table 3B show the rat PK data for Compounds 1, 3 and 5 following SC administration. The data for Compound 3 are shown in graphic form in FIG. 11.

TABLE 3A

SC Rat PK: EFdA Levels for EFdA and Compound 3

| | SC Comp 3 | SC Comp 3 | SC Comp 1 (EFdA) | SC Comp 1 (EFdA) |
|---|---|---|---|---|
| Dose of EFdA (mg/kg) | 10 | 100 | 100 | 10 |
| Excipients | 0.5% CMC-Na/ 0.5% TWEEN-80 | 0.25% CMC-Na/ 0.1% TWEEN-80 | 0.25% CMC-Na/ 0.1% TWEEN-80 | 0.5% CMC-Na/ 0.5% TWEEN-80 |
| Conc. of EFdA (mg/mL) | 4 | 120 | 319 | 4 |
| $T_{1/2}$ (h) | NA | 474 ± 168 | 99 ± 13 | 1.3 ± 0.2 |
| $MRT_{0\text{-}last}$ (h) | 20 ± 4 | 456 ± 17 | 67 ± 24 | 1.6 ± 0.1 |
| $T_{max}$ (h) | 4 ± 2.3 | 312 ± 0 | 1 ± 0 | 0.5 |
| $C_{max}$ (nM) | 287 ± 177 | 66 ± 21 | 7,429 ± 1,584 | 11,548 ± 3,173 |
| $AUC_{0\text{-}last}$ (nM*h) | 6,475 ± 2909 | 38,306 ± 101 | 158,500 ± 17 | 22,528 ± 1,680 |
| $AUC_{0\text{-}inf}$ (nM*h) | NA | 52,531 ± 39 | 159,373 ± 16 | 23,235 ± 2,000 |

TABLE 3B

SC Rat PK: EFdA Levels for EFdA and Compound 5

| | SC Comp 5 | SC Comp 1 (EFdA) |
|---|---|---|
| Dose of EFdA (mg/kg) | 100 | 100 |
| Excipients | 0.25% CMC-Na/0.1% TWEEN-80 | |
| Conc. of EFdA (mg/mL) | 116 | 319 |
| $T_{1/2}$ (h) | 363 ± 411 | 99 ± 13 |
| $MRT_{0\text{-}last}$ (h) | 225 ± 64 | 67 ± 24 |
| $C_{max}$ (nM) | 244 ± 54 | 7,429 ± 1,584 |
| $AUC_{0\text{-}last}$ (nM*h) | 68,848 ± 16,728 | 158,500 ± 17 |
| $AUC_{0\text{-}inf}$ (nM*h) | 129,209 ± 117,423 | 159,373 ± 16 |

Example 7

After rat PK analysis, the focus was shifted to non-rodents, i.e., rhesus macaque. Compound 5 and EFdA were subjected to a single dose rhesus macaque PK studies via subcutaneous route of administration with equivalent doses of 50 mg/kg of EFdA. The aqueous suspensions contained 0.25% CMC-Na and 0.1%/0.5% TWEEN-80 with equivalent concentration of 116 mg/mL and 319 mg/mL of EFdA for Compound 5 and EFdA respectively. With Compound 5 plasma levels of EFdA above LLOQ for more than a month with 24-fold lower $C_{max}$ than EFdA itself were observed.

Figure 12:
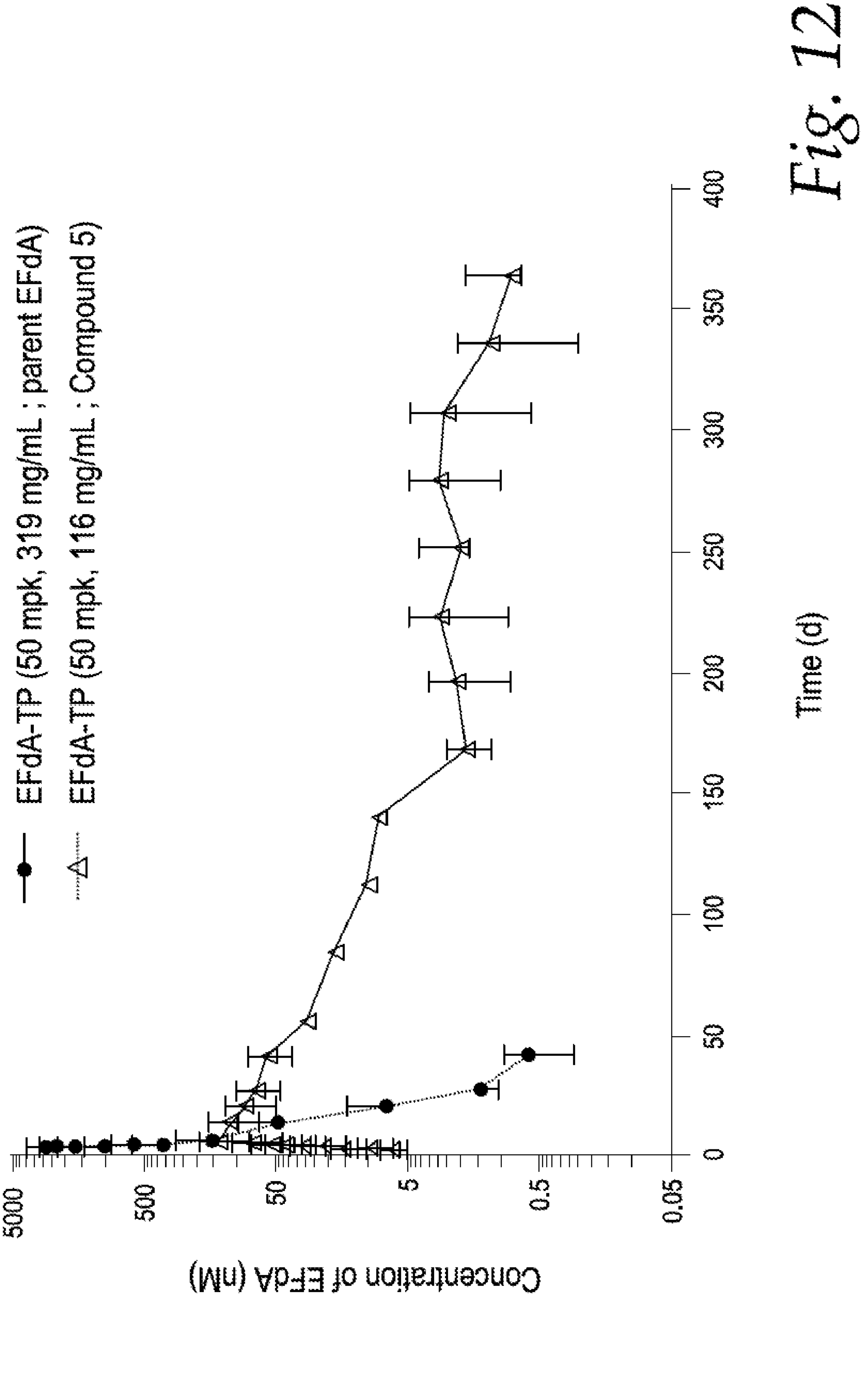
FIG. 12 shows in graphic form the data in Table 4.

Table 4 shows the Rhesus PK data for Compounds 1 and 5 following SC administration at 50 mg/kg equivalent dose of EFdA. The data are shown in graphic form in FIG. 12.

TABLE 4

SC Rhesus PK: EFdA Plasma Levels after Dosing EFdA or Compound 5 in Plasma

| | SC EFdA EFdA (Plasma) | SC Compound 5 EFdA (Plasma) |
|---|---|---|
| Dose of EFdA (mg/kg) | 50 | 50 |
| Excipients | 0.25% CMC-Na 0.1% TWEEN-80 | 0.25% CMC-Na 0.5% TWEEN-80 |
| Conc. of EFdA (mg/mL) | 319 | 116 |
| $T_{1/2}$ (h) | 165 ± 56 | 1,063 ± 608 |
| $MRT_{0\text{-}last}$ (h) | 79 ± 37 | 1,449 ± 517 |
| $T_{max}$ (h) | 4 ± 3.6 | 264 ± 125 |
| $C_{max}$ (nM) | 3,060 ± 1,058 | 128 ± 52 |
| $C_{42\ days}$ (nM) | 0.6 ± 0.3 | 60 ± 16 |
| $AUC_{0\text{-}last}$ (nM*h) | 135,691 ± 22,574 | 143,330 ± 33,727 |
| $AUC_{0\text{-}inf}$ (nM*h) | 135,748 ± 22,594 | 145,643 ± 32,180 |

Suspending medium for the present compounds can be an aqueous vehicle such as water for injection (WFI) or a vegetable oil vehicle such as sesame oil, olive oil, and the like. The suspending medium can also contain pharmaceutically acceptable excipients such as non-ionic surfactant, suspending or flocculating agent, preservatives, buffers, toxicity adjusters, chelating agents, antioxidants, and the like.

For prophylaxis, a preferred prophylactic dose for a human subject is in the range of about 80 mg to about 800 mg of the antiviral compound administered parenterally at about six-month (semi-annual) intervals in a dose volume of about 0.5 to about 4 milliliters (mL) per dose.

For treatment of a human patient, the effective amount of the antiviral compound of this invention preferably ranges from about 80 mg to about 800 mg at a dose volume of about 0.5 to about 4 mL per dose, more preferably an effective amount in the range of about 200 to about 400 mg, for a three-month dosage regimen. The dosage regimen can vary, however, depending on the time interval between administered doses in a particular dosing regimen.

The term "effective amount" as used herein and in the claims means an amount of the antiviral compound sufficient to inhibit HIV reverse transcriptase, inhibit HIV replication, exert a prophylactic effect and/or exert a therapeutic effect after administration.

The term "administration" and variants thereof, for example "administering a compound", with reference to the claimed method of treatment means providing the antiviral compound to the patient and includes self-administration as well as administration to the patient by another person.

Preferably, the parenteral suspensions suitable for injection contain the present antiviral compound in an amount in the range of about 3 to 45 percent by weight, based on the weight of the suspension. Preferred particle size is no greater than about 50 micrometers (μm), more preferably an average particle size in the range of about 6 μm to about 15 μm.

Preferred flocculating or suspending agents are linear polymers, particularly the substituted celluloses such as methyl cellulose, carboxymethyl cellulose (CMC), hyroxypropyl cellulose, hydroxypropylmethyl cellulose, and the like.

Preferred surfactants are non-ionic surfactants. Particularly preferred surfactant is polyoxyethlene (20) sorbitan monooleate (TWEEN-80).

In addition to parenteral dosage forms, the present compounds can also be administered in oral dosage forms and as implants.

Dosage forms containing the present compounds can also include additional anti-HIV and/or anti-HBV agents such as cabotegravir, dolutegravir, doravirine, evilegravir, lesiverine, tenofovir disoproxil fumarate, tenofovir alafenamide fumarate, lamivudine, and the like.

The invention further provides, in various embodiments, a method of prophylaxis of viremia or treatment of a viral infection in a patient wherein inhibition of a reverse transcriptase is medically indicated, comprising administering to the patient an effective amount or concentration of a compound of Formula (II). More specifically, the compound of Formula (II) can be administered in a formulation that provides for slow or controlled or sustained release of EFdA from these prodrugs. More specifically, the compound of Formula (II) can be formulated as aqueous suspension, solutions, and can be encapsulated in particles for slow-release including PLGA and other such materials known in the art. More specifically, the viral infection can be caused by HIV or HBV. The routes of administration for these prodrugs can include, but not limited to, oral, parenteral and release from implants (drug delivery composition and device). In the method for the treatment or prevention of the viral infection, the method may further comprise an additional anti-HIV and/or anti-HBV agent including but not limited to, cabotegravir, dolutegravir, doravirine, elvitegravir, lersiverine, tenofovir disoproxil fumarate, tenofovir alafenamide fumarate, lamivudine, and the like.

Example 8

The concentration of surfactant was optimized with 0.3% and 0.5% of methyl cellulose in a formation containing 400 mg/gm of micronized Compound 5. Formulations were prepared with different concentrations of TWEEN-80 (0.1, 0.2 and 0.3%). No significant effect of surfactant concentration was observed in viscosity, flow and redispersion time in the formulations after 10 days of storage. The observations are reported in Table 5.

TABLE 5

Optimization of Surfactant Concentration with 400 mg/gm of Compound 5

| Composition | Surfactant Conc. TWEEN-80 | Syringe-ability (26 G) | Viscosity | Flow | Time Taken to Resuspend |
|---|---|---|---|---|---|
| 0.3% Methyl Cellulose | 0.1% | ✓ | ++++ | ++++ | 2.2 Min. |
| | 0.2% | ✓ | ++++ | ++++ | 2.5 Min. |
| | 0.3% | ✓ | ++++ | ++++ | 2.3 Min |
| 0.5% Methyl Cellulose | 0.1% | ✓ | ++++ | ++++ | 2.5 Min. |
| | 0.2% | ✓ | ++++ | ++++ | 2.5 Min. |
| | 0.3% | ✓ | ++++ | ++++ | 3.0 Min. |

Viscosity:
++++ Slightly Viscous,
+++ Viscous,
++ Very Viscous,
+ Semisolid
Flow:
+ No Flow,
++ Less Flow,
+++ Good Flow,
++++ Very Good Flow
✓: Syringeable Example 9

A bulk batch (40 gm) of Compound 5 suspension was prepared with 0.3% methyl cellulose and 0.2% TWEEN-80 concentration. Although the polymer and surfactant concentrations were optimized with 40 weight % of drug concentration, a bulk batch was also prepared with 35 weight % of drug concentration during accelerated and long term stability studies. The composition of formulation loaded in stability chamber is given in Table 6. A detailed manufacturing procedure of formulation preparation and composition is given below.

TABLE 6

Formulation Composition

| Ingredient | Quantity (mg/g) | Quantity, g/40 g |
|---|---|---|
| Compound 5 | 350 | 14 |
| Methyl Cellulose | 3 | 0.120 |
| TWEEN-80 | 2 | 0.08 |
| Water for Injection (WFI) | 645 | 25.8 |

Methyl cellulose was slowly added to the requisite quantity of water for injection (WFI) in a glass bottle with continuous stirring. The resulting mixture was stirred until the solution was clear and free from any lumps using a magnetic stirrer. TWEEN-80 (0.08 g) was added to the obtained solution and stirred well.

Micronized Compound 5 (14 g; average particle size 11 μm) was slowly added to the prepared polymer, surfactant solution under vigorous stirring at 1400 rpm using a magnetic stirrer. After complete addition of Compound 5, the obtained suspension was stirred (600 rpm) for 20 minutes to uniformly disperse the particles.

The prepared formulation was characterized for various physicochemical properties such as assay, pH, % purity, redispersability, injectability, polymorphic form and particle size. The results are presented in Table 7.

TABLE 7

| Physicochemical Characterization of Formulation on Preparation | |
|---|---|
| Test Parameter | |
| Appearance | White dispersion |
| pH | 5.78 |
| Assay by HPLC (% on label claim) | 108.8% |
| % Purity | 99.34% |
| Redispersability | Yes |
| Injectability | Yes |
| Polymorphic Form | Same as API |
| Average Particle Size | 14 μm |

The formulation shown in Table 6 was deemed acceptable based on the characteristics shown in Table 7.

Example 10

Figure 13:
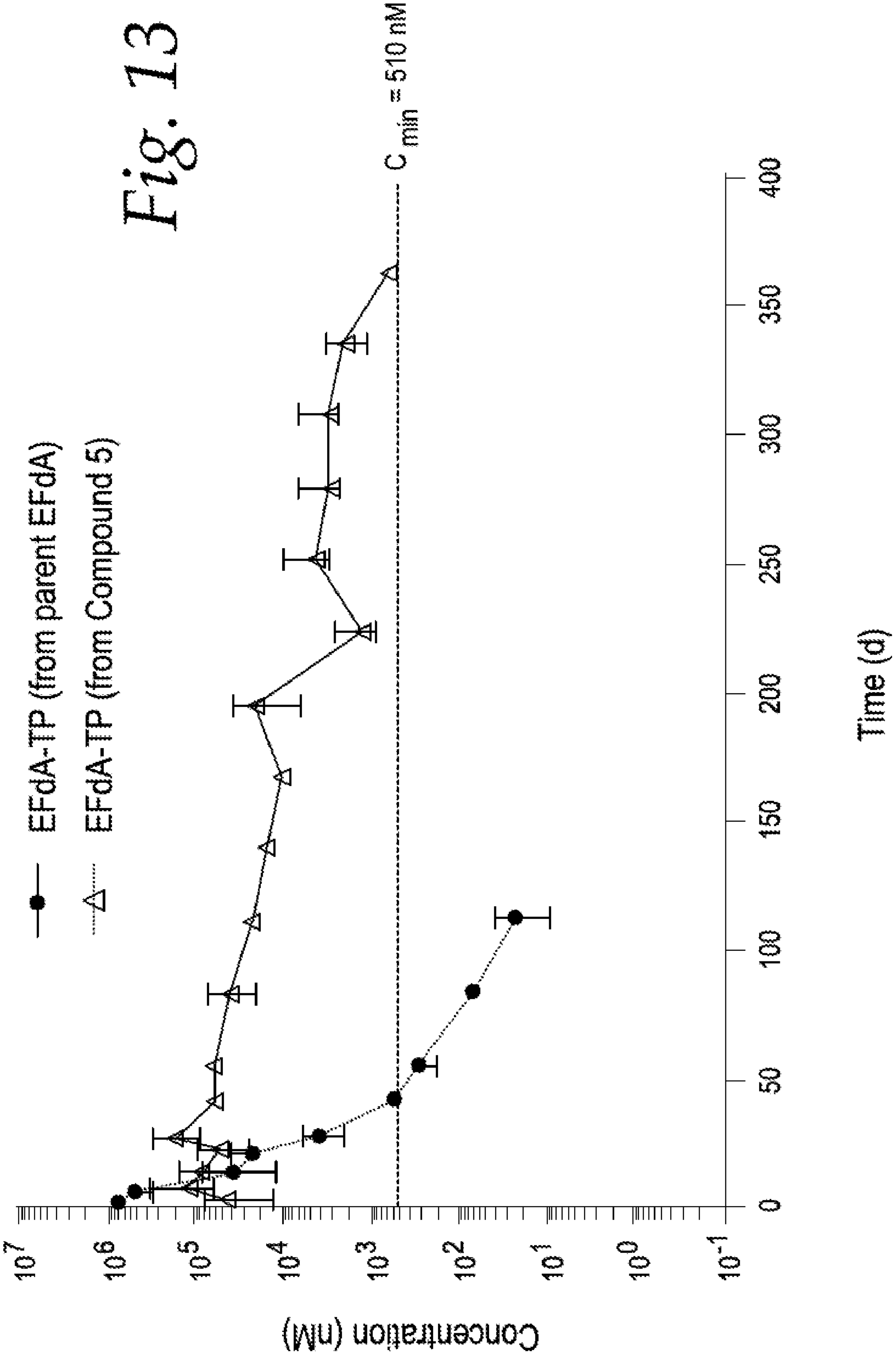
FIG. 13 shows in graphic form data from Example 10.

Aqueous suspensions of EFdA and of Compounds 3 and 5 were administered subcutaneously to Rhesus Macaque, peripheral blood mononuclear cells (PBMC) periodically retrieved, and pharmacokinetic data evaluated. The observed results are presented in Tables 8, 9, and 10, for both compounds, and in FIG. 13 for Compound 5.

TABLE 8

SC Rhesus PK: EFdA-TP PBMC Levels After Dosing Compound 5 or EFdA

| | SC Compound 5: EFdA-TP (PBMC) | SC EFdA: EFdA-TP (PBMC) |
|---|---|---|
| EFdA Nominal Dose (mg/kg) | 50 | 50 |
| Formulation | 0.25% CMC-Na/0.5% TWEEN-80 | 0.25% CMC-Na/0.1% TWEEN-80 |
| Conc. of EFdA (mg/mL) | 116 | 319 |
| Dose volume (mL/kg) | 0.43 (tot. vol. 1.39 mL) | 0.16 (tot. vol. 0.47 mL) |
| $T_{1/2}$ (d) | 31 ± 17 | 12 ± 5 |
| MRT $_{0\text{-}last}$ (d) | 72 ± 19 | 6 ± 1 |
| MRT $_{0\text{-}inf}$ (d) | 73 ± 21 | 6 ± 1 |
| $T_{max}$ (d) | 21 ± 13 | 2 ± 0 |
| $C_{max}$ (μM) | 192 ± 96 | 789 ± 154 |
| $C_{last}$ (μM) | 0.71 | 0.03 |
| $AUC_{0\text{-}last}$ (μM*h) | 233,2743 ± 37,553 | 127,176 ± 29,205 |
| $AUC_{0\text{-}inf}$ (μM*h) | 234,062 ± 37,077 | 127,201 ± 29,225 |

TABLE 9

SC Rhesus PK: EFdA Plasma and EFdA-TP PBMC Levels After Dosing Compound 3

| | SC Compound 3: EFdA (Plasma) | SC Compound 3: EFdA-TP (PBMC) |
|---|---|---|
| EFdA Nominal Dose (mg/kg) | 50 | |
| Formulation | 0.25% CMC-Na/0.5%TWEEN80 | |
| Conc. of EFdA (mg/mL) | 150 | |
| Dose volume (mL/kg) | 0.335 (tot. vol. 1.57 mL) | |
| $T_{1/2}$ (h) | 566 ± 344 | 1,022 ± 463 |
| $MRT_{0\text{-}last}$ (h) | 1,071 ± 488 | 394 ± 36 |
| $T_{max}$ (h) | 440 ± 270 | 784 ± 485 |
| $C_{max}$ (M) | 40 ± 28 | 627 ± 60 |
| $AUC_{0\text{-}last}$ (nM*h) | 35,385 ± 18,522 | 807,473 ± 519,381 |
| $AUC_{0\text{-}inf}$ (nM*h) | 45,293 ± 14,840 | 1,447,998 ± 576,163 |

TABLE 10

SC Rhesus PK: EFdA Levels for Compounds 3 and 5 in Plasma

| | SC EFdA EFdA (Plasma) | SC Compound 5: EFdA (Plasma) | SC Compound 3: EFdA (Plasma) |
|---|---|---|---|
| EFdA Nominal Dose (mg/kg) | 50 | 50 | 50 |
| Formulation | 0.25% CMC-Na/ 0.1% Tween 80 | 0.25% CMC-Na/ 0.5% Tween 80 | 0.25% CMC-Na/ 0.5% Tween 80 |
| Conc. of EFdA (mg/mL) | 319 | 116 | 150 |
| $T_{1/2}$ (h) | 165 ± 56 | 1,063 ± 608 | 566 ± 344 |
| $MRT_{0\text{-}last}$ (h) | 79 ± 37 | 1,449 ± 517 | 1,071 ± 488 |
| $T_{max}$ (h) | 4 ± 3.6 | 264 ± 125 | 440 ± 270 |
| $C_{max}$ (nM) | 3060 ± 1058 | 128 ± 52 | 40 ± 28 |
| $AUC_{0\text{-}last}$ (nM*h) | 135,691 ± 22,574 | 143,330 ± 33,727 | 35,385 ± 18,522 |
| $AUC_{0\text{-}inf}$ (nM*h) | 135,748 ± 22,594 | 145,643 ± 32,180 | 45,293 ± 14,840 |

We claim:

1. A compound, which is:

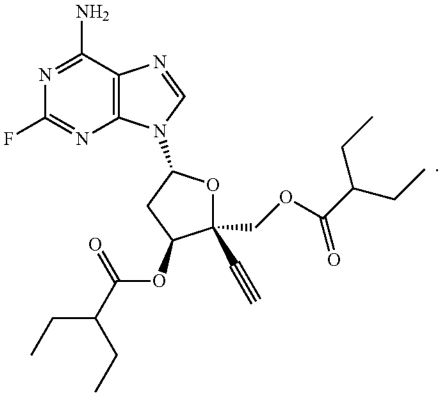 [SMILES: C#C[C@]1(COC(=O)C(CC)CC)O[C@@H](n2cnc3c(N)nc(F)nc32)C[C@@H]1OC(=O)C(CC)CC]

2. A compound, which is:

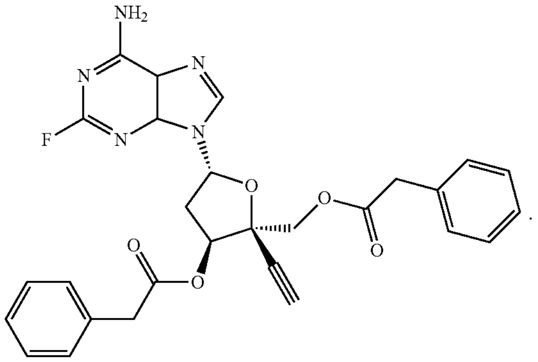 [SMILES: C#C[C@]1(COC(=O)Cc2ccccc2)O[C@@H](N2C=NC3C(N)=NC(F)=NC32)C[C@@H]1OC(=O)Cc1ccccc1]

* * * * *